(12) United States Patent
Dasbach et al.

(10) Patent No.: US 11,612,695 B2
(45) Date of Patent: Mar. 28, 2023

(54) DRUG DELIVERY DEVICE

(71) Applicant: Sanofi-Aventis Deutschland GMBH, Frankfurt am Main (DE)

(72) Inventors: Uwe Dasbach, Frankfurt am Main (DE); Marc Schader, Frankfurt am Main (DE); Michael Kneip, Frankfurt am Main (DE); Matthias Rau, Rüsselsheim (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 447 days.

(21) Appl. No.: 16/493,505

(22) PCT Filed: Mar. 12, 2018

(86) PCT No.: PCT/EP2018/056111
§ 371 (c)(1),
(2) Date: Sep. 12, 2019

(87) PCT Pub. No.: WO2018/166985
PCT Pub. Date: Sep. 20, 2018

(65) Prior Publication Data
US 2021/0162133 A1 Jun. 3, 2021

(30) Foreign Application Priority Data

Mar. 13, 2017 (EP) ..................................... 17160487

(51) Int. Cl.
*A61M 5/315* (2006.01)
*A61M 5/20* (2006.01)

(52) U.S. Cl.
CPC . *A61M 5/31511* (2013.01); *A61M 2005/2086* (2013.01); *A61M 2205/581* (2013.01); *A61M 2205/582* (2013.01); *A61M 2207/00* (2013.01)

(58) Field of Classification Search
CPC .......... A61M 5/31511; A61M 5/31501; A61M 5/3272; A61M 5/347; A61M 2005/2086; A61M 2205/581; A61M 2205/582
See application file for complete search history.

(56) References Cited

U.S. PATENT DOCUMENTS

| 10,960,139 B2 * | 3/2021 | Schiff | ................ A61M 5/31511 |
| 2005/0222539 A1 * | 10/2005 | Gonzales | ............ A61M 5/3157 604/207 |

(Continued)

FOREIGN PATENT DOCUMENTS

| CN | 2701455 Y | 5/2005 |
| CN | 102361660 | 2/2012 |

(Continued)

OTHER PUBLICATIONS

International Preliminary Report on Patentability in International Application No. PCT/EP2018/056111, dated Sep. 17, 2019, 7 pages.

(Continued)

*Primary Examiner* — Nathan R Price
*Assistant Examiner* — Justin L Zamory
(74) *Attorney, Agent, or Firm* — Fish & Richardson P.C.

(57) ABSTRACT

The present disclosure relates to a drug delivery device, having a longitudinal axis and comprising a plunger movable along the longitudinal axis and a guide curve adapted to engage at least one part of the plunger so as to guide the plunger when the plunger is being released to move along the longitudinal axis.

24 Claims, 26 Drawing Sheets

(56) References Cited

U.S. PATENT DOCUMENTS

| | | | |
|---|---|---|---|
| 2010/0185178 A1 | 7/2010 | Sharp et al. | |
| 2011/0224643 A1 | 9/2011 | Schliemann et al. | |
| 2013/0102969 A1* | 4/2013 | Veasey .............. | A61M 5/31551 |
| | | | 604/189 |
| 2014/0124542 A1 | 5/2014 | Kojima et al. | |
| 2016/0144129 A1* | 5/2016 | Mosebach ......... | A61M 5/31585 |
| | | | 604/193 |

FOREIGN PATENT DOCUMENTS

| | | |
|---|---|---|
| CN | 105517599 | 4/2016 |
| CN | 106061529 | 10/2016 |
| CN | 106068135 | 11/2016 |
| EP | 2383005 | 11/2011 |
| EP | 2823841 | 1/2015 |
| JP | 2016-523672 | 8/2016 |
| WO | WO 2005/097238 | 10/2005 |
| WO | WO 2010/084306 | 7/2010 |
| WO | WO 2012/147862 | 11/2012 |
| WO | WO 2015/004052 | 1/2015 |
| WO | WO 2015/121080 | 8/2015 |
| WO | WO 2015/132234 | 9/2015 |
| WO | WO 2018/166985 | 9/2018 |

OTHER PUBLICATIONS

International Search Report and Written Opinion in International Application No. PCT/EP2018/056111, dated Jul. 2, 2018, 9 pages.

* cited by examiner

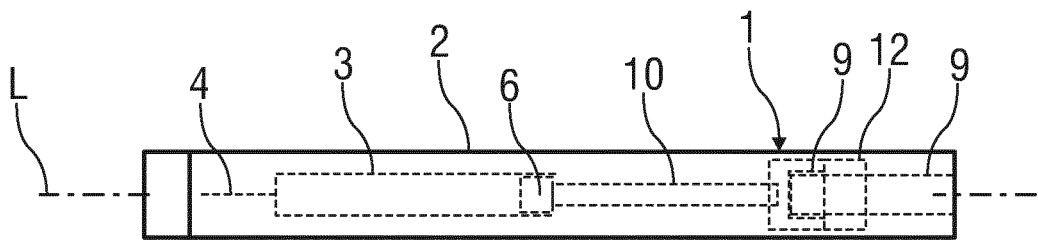
FIG 1A
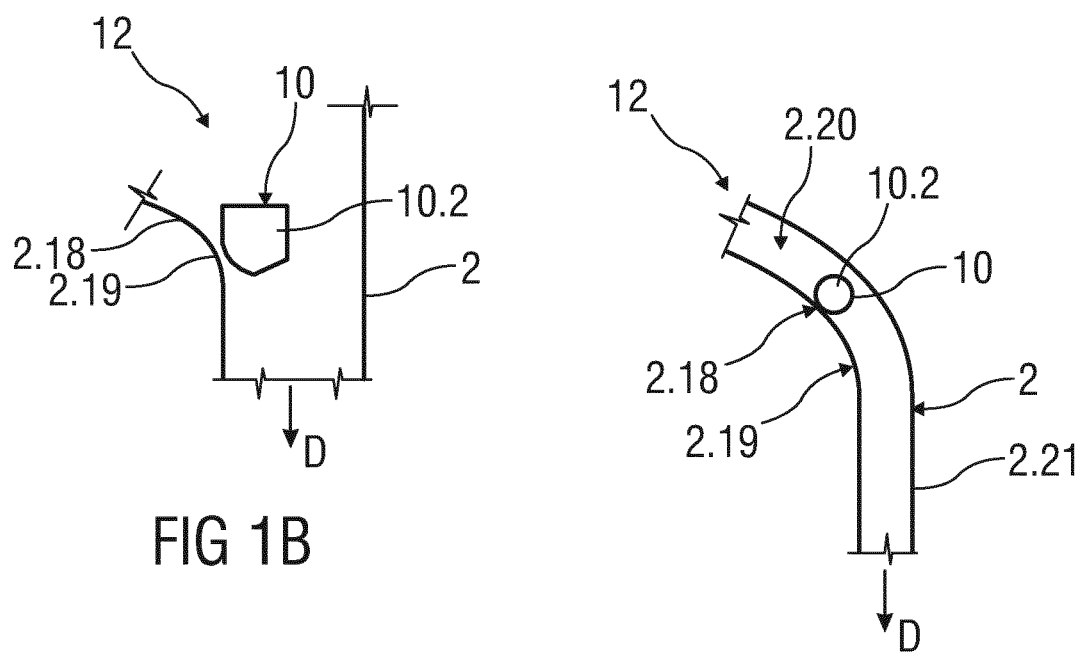
FIG 1B
FIG 1C

DRUG DELIVERY DEVICE

CROSS-REFERENCE TO RELATED APPLICATIONS

The present application is the national stage entry of International Patent Application No. PCT/EP2018/056111, filed on Mar. 12, 2018, and claims priority to European Application No. 17160487.9, filed on Mar. 13, 2017, the disclosures of which are incorporated herein by reference.

TECHNICAL FIELD

The disclosure generally relates to a drug delivery device.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

EP 2 823 841 A1 discloses an autoinjector having a plunger release mechanism which comprises a sharp or step edge for interaction with the plunger to provide an audible feedback indicating that delivery of the medicament has started. WO 2005/097238 A2 discloses an injector device having a release apparatus comprising shoulders of resilient bifurcated section. The shoulders engage an end of the body and thus maintain the drive member locked in an unreleased position. The shoulders have a cam surface which interacts with corresponding cam surface in the release apparatus for releasing the drive member and spring. US 2010/185178 A1 discloses an injection device wherein the plunger is constrained against rotation relative to the syringe housing.

There remains a need for an improved drug delivery device.

SUMMARY

The present disclosure describes an improved drug delivery device.

According to the present disclosure, a drug delivery device has a longitudinal axis and comprises a plunger release mechanism comprising at least a plunger movable along the longitudinal axis and a guide curve adapted to engage at least one part of the plunger so as to guide the plunger, in particular impact-free or shock-free when the plunger is being released to move along the longitudinal axis. The plunger may thus be prevented from rotating or be rotated in a defined way while being moved along the longitudinal axis.

In some embodiments, the guide curve is configured such that the guiding of the plunger is free from any impact or bump on other parts of the device. In particular, the guide curve is configured to damp or slow down the movement of the plunger by friction. For instance, a curve surface of the guide curve may comprise a coating.

In some embodiments, the drug delivery device comprises a case adapted to contain a container having a hollow injection needle and a stopper. The drug delivery device further comprises a drive spring and the plunger that is adapted to forward load of the drive spring to the stopper. The guide curve is configured to damp or slow down the movement of the plunger while the drive spring expands and its force decreases onto the plunger.

In some embodiments, the guide curve and the part of the plunger are interrelated and interacting with each other. In particular, the guide curve may be rounded in a predetermined angle or may comprise a convex surface. Furthermore, the part of the plunger guided by the guide curve may be rounded correspondingly or may comprise a convex surface.

In some embodiments, the guide curve is configured such that the part of the plunger initially is maintained in engagement with the guide curve and finally disengages from the guide curve.

In some embodiments, the guide curve is a one-sided curve. In other words: The guide curve is not part of a slot. In particular, the one-sided guide curve is formed on an outer surface of a part of the injection device which is arranged opposite to the part of the plunger which is being to guide within the device.

Alternatively, the guide curve may be formed as a curved slot or a part of a slot. The slot or a part of the slot is configured such that the part of the plunger which is being to guide engages only one of the slot surfaces, e.g. an inner curved slot surface and does not come into contact with the opposite, e.g. an outer curved slot surface.

In some embodiments, the drug delivery device further comprises a case and/or a sleeve, wherein the guide curve is arranged on the case and/or on the sleeve. The plunger may thus be prevented from rotating or be rotated relative to the case and/or sleeve in a defined way while being moved along the longitudinal axis.

In some embodiments, the guide curve comprises a curved section. The plunger may thus be rotated in a defined way while being moved along the longitudinal axis. This may be used to adapt the movement of the plunger to a force profile of a drive mechanism, e.g. a drive spring, in particular to achieve movement of the plunger with a substantially constant force while the drive spring expands and its force decreases. The curved section may also be used to transition rotation of the plunger about the longitudinal axis into translation along the longitudinal axis or vice versa. Due to the transition of the plunger rotation into translation along the longitudinal axis, a part of the plunger, e.g. a part engaged to the guide curve or another part extending radially outwards, is inhibited from impacting other components, e.g. the case or sleeve, so that an audible and/or tactile feedback due to the impact during rotation of the plunger, which may for example occur when the plunger is released, is prevented or mitigated. Such an audible and/or tactile feedback may be confusing for some users as they might interpret this to indicate an end of dose.

In some embodiments, the plunger comprises a first plunger boss extending radially outwards from the plunger, wherein the case comprises a case slot adapted to engage the first plunger boss so as to inhibit or restrict movement of the plunger along the longitudinal axis, wherein the plunger is configured to be rotated such that the first plunger boss disengages the case slot thus releasing the plunger for axial translation, wherein the curved section is arranged to engage at least one part of the plunger during and/or after disengagement of the plunger boss from the case slot.

In some embodiments, the case slot comprises a surface adapted to engage the first plunger boss so as to inhibit axial translation, wherein the surface is rounded off at an end in a rotational direction in which the plunger is configured to rotate out of engagement with the case slot such that the rounded off end of the surface forms an inside of a turn of the curved section configured to be engaged by the part of the plunger being the first plunger boss.

In some embodiments, the curved section comprises an outside of a turn configured to engage the at least one part of the plunger. Rotational play of the plunger during release is thus limited. The part of the plunger engaging the outside of the turn may be the same as or a different one as the part of the plunger engaging the inside of the turn.

In some embodiments, the first plunger boss is rounded off at least in a region configured to engage the inside turn of the curved section.

In some embodiments, the curved section extends over such a length of the guide curve that the plunger is rotated only prior to abutting a stopper of a medicament container arrangeable in the drug delivery device. The curved section may have an extent such that the plunger transitions between rotation and translation when travelling only a relatively short axial distance, wherein a gap may be provided between the plunger and the stopper when the first plunger boss is engaged in the case slot, the gap being long enough that the plunger has stopped rotating before engaging the stopper so that the stopper is not subjected to torque. Subjection of the stopper to torque which may result in friction, is thus avoided.

In some embodiments, the curved section extends over such a length of the guide curve that the plunger is rotated during most of its axial translation.

In some embodiments, the guide curve comprises the shape of a part of a parabola.

In some embodiments, the at least one part of the plunger is engaged to a vertex of the parabola when the first plunger boss is engaged in the case slot. The part of the plunger may then move along the parabola away from the vertex when the plunger has been released so that the plunger primarily rotates when the first plunger boss disengages the case slot and then increasingly translates as the speed of rotation decreases.

In some embodiments, a bearing is arranged on a distal end of the plunger for engaging a stopper of a medicament container. The bearing may be arranged to allow free rotation of a distal tip of the plunger relative to the rest of the plunger about the longitudinal axis such that rotation of the plunger does not rotate the stopper or subject it to torque. The bearing may be a ball bearing or a slide bearing. The bearing may be integral with the plunger or be arranged as a separate part.

In some embodiments, the surface of the case slot, adapted to engage the first plunger boss, is angled so as to induce a torque to the plunger when an axial force is applied to the plunger, e.g. by a user, by a drive spring or by a linear actor. This may facilitate release of the plunger to start a drug delivery.

In some embodiments, the drug delivery device further comprises a medicament container having a stopper adapted to be engaged by the plunger.

In some embodiments, the medicament container contains a medicament.

The curved section and the first plunger boss may comprise materials increasing friction between the curved section and the first plunger boss in order to prevent the plunger boss from prematurely disengaging the curved section. Likewise, a radius of the curved section may be varied or the curved section may be flattened to achieve this.

In some embodiments, the plunger release mechanism further comprises a needle shroud, wherein the plunger comprises a second plunger boss, wherein a shroud rib is arranged on the needle shroud adapted to engage the second plunger boss to inhibit rotation of the plunger when the needle shroud is in an extended position and adapted to disengage the first plunger boss when the needle shroud is in a retracted position. The first plunger boss may thus be prevented from disengaging the angled surface of the case slot as long as the needle shroud is not moved into the retracted position, e.g. by being pressed against an injection site.

In some embodiments, the plunger release mechanism further comprises a plunger rib on the plunger adapted to interact with the shroud rib so as to rotate the first plunger boss out of the case slot when the needle shroud is axially moved against the plunger in a proximal direction. This may be applied to support rotation or actively rotate the plunger out of engagement with the case slot even if the surface of the case slot adapted to engage the first plunger boss is not angled.

In some embodiments, the shroud rib comprises a distal face adapted to engage the second plunger boss so as to limit movement of the needle shroud in a distal direction relative to the plunger.

In some embodiments, a shroud spring is arranged to bias the needle shroud in a distal direction against the case.

In some embodiments, a drive spring is arranged within a proximal part of the case and configured to bias the plunger in the distal direction for displacing a stopper disposed in a syringe.

In some embodiments, the drug delivery device may be an autoinjector.

According to an aspect of the present disclosure, a method of manufacturing a drug delivery device comprises the steps of:
providing a plunger movable along a longitudinal axis,
providing a guide curve, and
assembling the plunger and the guide curve such that the guide curve engages at least one part of the plunger so as to guide the plunger when the plunger is being moved along the longitudinal axis.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 1A is a schematic view of an embodiment of a drug delivery device comprising a release mechanism according to the present disclosure;

FIG. 1B is a schematic view of an embodiment of a release mechanism;

FIG. 1C is a schematic view of another embodiment of a release mechanism;

Corresponding parts are marked with the same reference symbols in all figures.

DETAILED DESCRIPTION

Figure 1D:
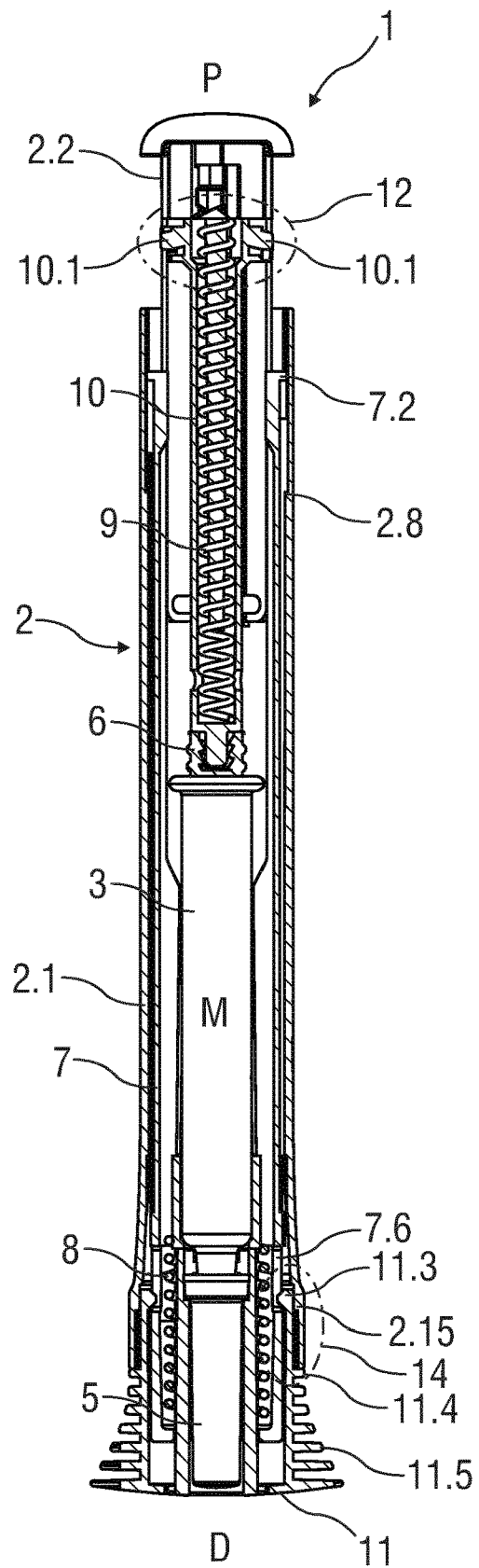
FIG. 1D is a longitudinal section of an embodiment of a drug delivery device according to the present disclosure during assembly.

FIG. 1A shows an exemplary embodiment of a drug delivery device 1 having a longitudinal axis L. The device 1 may configure as an auto-injector.

The device 1 comprises a plunger release mechanism 12.

The plunger release mechanism 12 comprises at least a plunger 10 movable along the longitudinal axis L and a guide curve 2.18 adapted to engage at least one part of the plunger 10 so as to guide the plunger 10 when the plunger 10 is being released to move along the longitudinal axis L. The plunger 10 may thus be prevented from rotating or be rotated in a defined way while being moved along the longitudinal axis L.

According to the disclosure, the guide curve 2.18 guides the at least one part of the plunger 10 impact-free or shock-free when the plunger 10 is being released.

In some embodiments, the drug delivery device 1 comprises a case 2 adapted to contain a container 3, e.g. a pre-filled syringe (the container is further mentioned as syringe 3) having a hollow injection needle 4 and a stopper 6. The drug delivery device 1 further comprises a drive spring 9 and the plunger 10 which is adapted to forward load of the drive spring 9 to the stopper 6. The guide curve 2.18 is configured to damp or slow down the movement of the plunger 10 while the drive spring 9 expands and its force decreases onto the plunger 10.

FIG. 1B shows an embodiment of the plunger release mechanism 12. The guide curve 2.18 is configured such that the guiding of the plunger 10 is free from any impact or bump on other parts of the device 1. In particular, the guide curve 2.18 is configured to damp or slow down the movement of the plunger 10 by friction. For instance, a curve surface of the guide curve 2.18 may comprise a coating.

In some embodiments, the guide curve 2.18 and the part of the plunger 10, in particular a first plunger boss 10.2 are interrelated and interacting with each other. In particular, the guide curve 2.18 may be rounded in a predetermined angle or may comprise a convex surface. Furthermore, the part of the plunger 10 guided by the guide curve 2.18 may be rounded correspondingly or may comprise a convex surface.

In some embodiments, the guide curve 2.18 is configured such that the part of the plunger 10 initially is maintained in engagement with the guide curve 2.18 and finally disengages from the guide curve 2.18.

In some embodiments, the guide curve 2.18 is a one-sided curve. In other words: The guide curve 2.18 is not part of a slot. In particular, the one-sided guide curve 2.18 is formed on an outer surface of a part of the drug delivery device 1 which is arranged opposite to the part of the plunger 10 which is being to guide within the device 1.

In particular, the guide curve 2.18 comprises a curved section 2.19 slowing down movement of the plunger 10 by friction such that the plunger 10 smoothly moves from rotating into translating in a distal direction D instead of rotating, impacting the case 2 and then translating in the distal direction D.

FIG. 1C shows another embodiment of the plunger release mechanism 12. A guide curve 2.18 may be formed as a curved slot 2.20 or a part of a slot 2.20. The slot 2.20 or a part of the slot 2.20 is configured such that the part of the plunger 10 which is being to guide engages only one of the slot surfaces, e.g. an inner curved slot surface and does not come into contact with the opposite, e.g. an outer curved slot surface 2.21 and/or the case 2.

FIG. 1D is a longitudinal section of an embodiment of a drug delivery device 1 according to the present disclosure during assembly. The drug delivery device 1 comprises a case 2 comprising a front case 2.1 and a rear case 2.2. The case 2 is adapted to hold a medicament container, such as a syringe 3. The syringe 3 may be a pre-filled syringe and have a needle 4 arranged at a distal end. When the drug delivery device 1 and/or the syringe 3 are assembled, a protective needle sheath 5 may be removably coupled to the needle 4. The protective needle sheath 5 may be a rubber needle sheath or a rigid needle sheath (which is composed of rubber and a full or partial plastic shell). A stopper 6 is arranged for sealing the syringe 3 proximally and for displacing a medicament M contained in the syringe 3 through the needle 4. In some embodiments, the medicament container may be a cartridge which includes the medicament M and engages a removable needle (e.g., by threads, snaps, friction, etc.).

In some embodiments, a cap 11 may be removably disposed at a distal end of the case 2. The cap 11 may include an element (e.g., a barb, a hook, a narrowed section, etc.) arranged to engage the protective needle sheath 5, the case 2 and/or a needle shroud 7 telescoped within the case 2. The cap 11 may comprise grip features 11.5 for facilitating removal of the cap 11 (e.g., by twisting and/or pulling the cap 11.5 relative to the case 2).

In some embodiments, a shroud spring 8 is arranged to bias the needle shroud 7 in a distal direction D against the case 2.

In some embodiments, a drive spring 9 is arranged within the case 2. A plunger 10 serves for forwarding a force of the drive spring 9 to the stopper 6. In some embodiments, the plunger 10 is hollow and the drive spring 9 is arranged within the plunger 10 biasing the plunger 10 in the distal direction D against the case 2. In some embodiments, the plunger 10 may be solid and the drive spring 9 may engage a proximal end of the plunger 10. Likewise, the drive spring 9 could be wrapped around the outer diameter of the plunger 10 and extend within the syringe 3.

In some embodiments, a plunger release mechanism 12 is arranged for preventing release of the plunger 10 prior to retraction of the needle shroud 7 relative to the case 2 and for releasing the plunger 10 once the needle shroud 7 is sufficiently retracted.

In some embodiments, a first shroud lock mechanism 14 is arranged to prevent retraction of the needle shroud 7 relative to the case 2 when the cap 11 is in place, thereby avoiding unintentional activation of the drug delivery device 1 (e.g., if dropped, during shipping or packaging, etc.). The first shroud lock mechanism 14 may comprise one or more compliant beams 11.3 on the cap 11 and a respective number of apertures 7.6 in the needle shroud 7 adapted to receive each of the compliant beams 11.3. When the cap 11 is attached to the drug delivery device 1, the compliant beams 11.3 abut a radial stop 2.15 on the case 2 which prevents the compliant beams 11.3 from disengaging the apertures 7.6. When the cap 11 is attached to the drug delivery device 1, axial movement of the cap 11 in a proximal direction P relative the case 2 is limited by a rib 11.4 on the cap 11 abutting the case 2. When the cap 11 is pulled in the distal direction D relative to the case 2, the compliant beams 11.3 may abut an edge of the aperture 7.6 and deflect to disengage the aperture 7.6, allowing for removal of the cap 11 and the protective needle sheath 5 attached thereto. In some embodiments, the compliant beams 11.3 and/or the apertures 7.6 may be ramped to reduce force necessary to disengage the compliant beams 11.3 from the apertures 7.6.

Figure 1E:
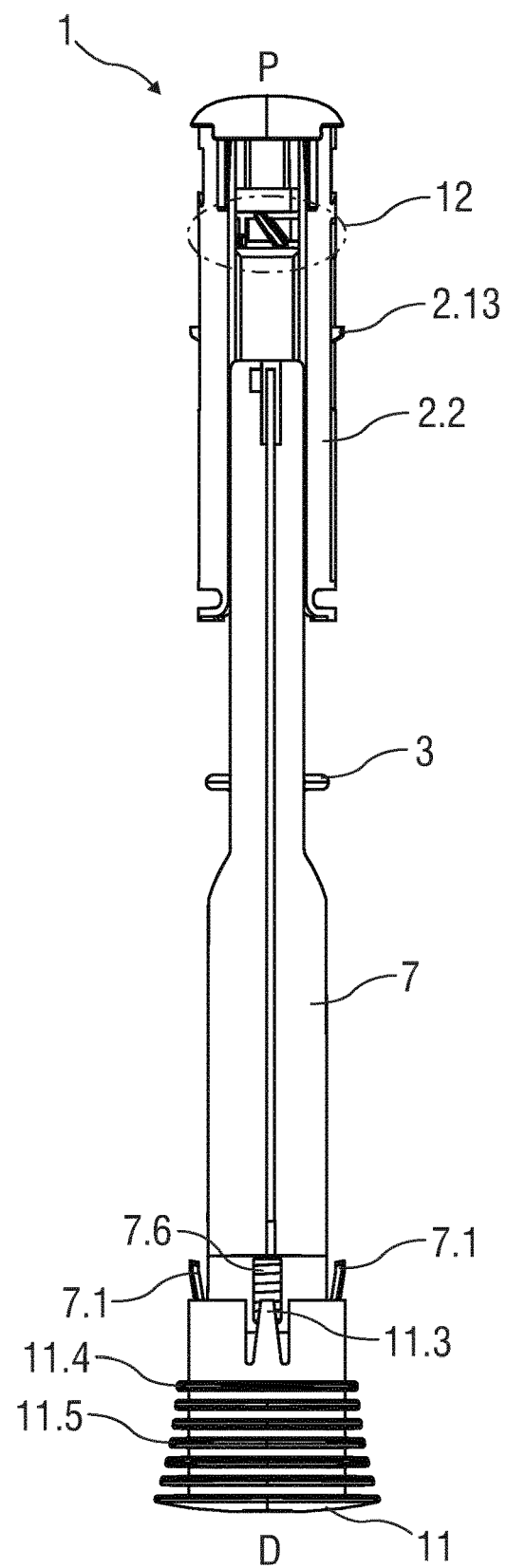
FIG. 1E is a schematic side view of an embodiment of a drug delivery device according to the present disclosure during assembly.
Figure 2:
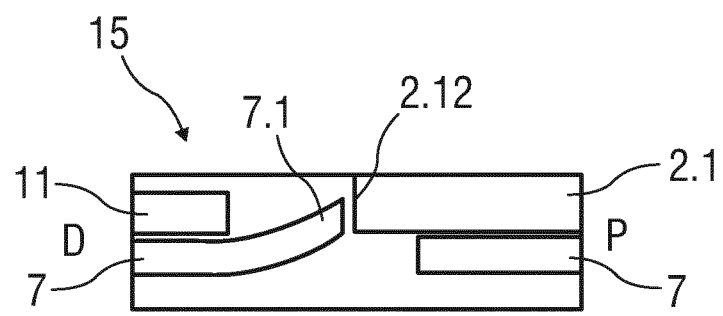
FIG. 2 is a schematic view of an embodiment of a shroud lock mechanism of an embodiment of a drug delivery device according to the present disclosure.

FIG. 1E is a schematic side view of an embodiment of the drug delivery device 1 according to the present disclosure during assembly. In the embodiment illustrated in FIG. 1B, the case 2 is removed for clarity. FIG. 1B and FIG. 2 show a second shroud lock mechanism 15 that is adapted to lock the needle shroud 7 in an axial position relative to the case 2 after the drug delivery device 1 has been removed from the injection site. In some embodiments, the second shroud lock mechanism 15 comprises at least one compliant shroud beam 7.1 on the needle shroud 7 adapted to proximally abut a stop 2.12 on the case 2 after the drug delivery device 1 has been removed from the injection site. The abutment of the shroud beam 7.1 on the stop 2.12 prevents translation of the needle shroud 7 in the proximal direction P relative to the case 2. Prior to use, when the cap 11 is attached to the drug delivery device 1, the cap 11 is adapted to engage and deflect the compliant shroud beam 7.1 radially inward, allowing the shroud beam 7.1 to pass the stop 2.12 in the proximal direction P so that the needle shroud 7 can translate in the proximal direction P relative to the case 2.

In some embodiments, the drug delivery device 1 may be formed from at least two subassemblies, e.g., a control subassembly 1.1 and a drive subassembly 1.2, to allow for flexibility as to the time and location of manufacture of the subassemblies 1.1, 1.2 and final assembly with the syringe 3.

Figure 3:
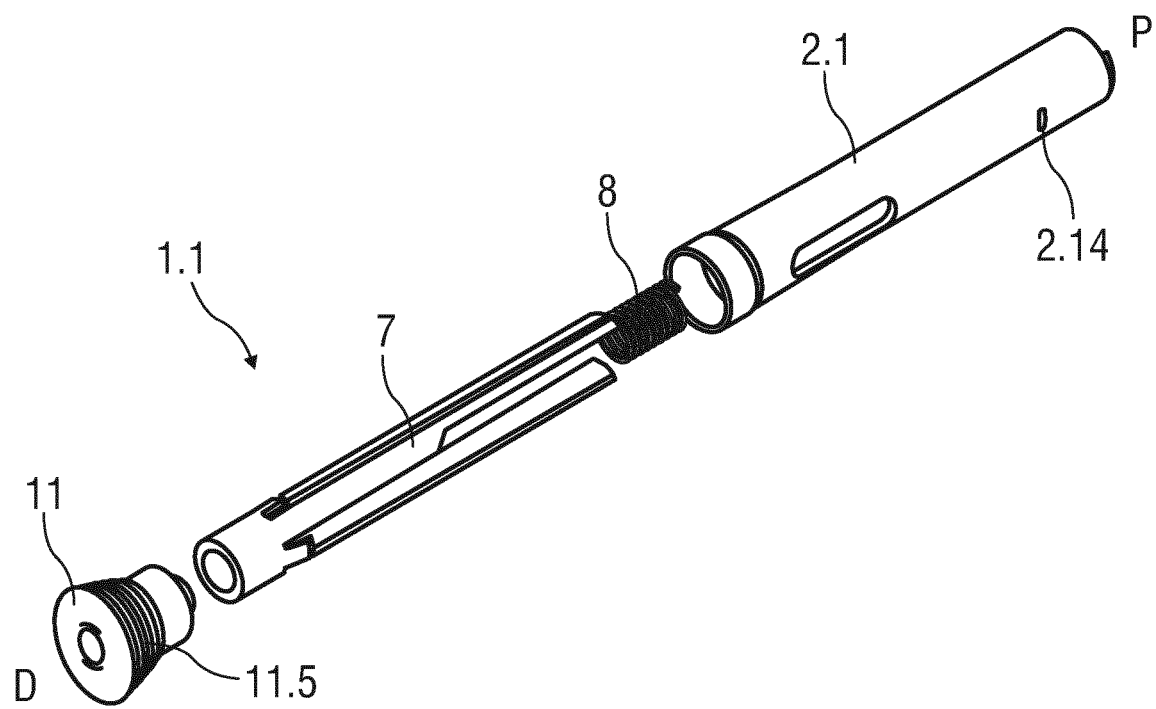
FIG. 3 is a perspective exploded view of an embodiment of a control subassembly of an embodiment of a drug delivery device according to the present disclosure.

FIG. 3 is a perspective exploded view of an embodiment of a control subassembly 1.1 of a drug delivery device 1 according to the present disclosure. In some embodiments, the control subassembly 1.1 comprises the cap 11, the needle shroud 7, the shroud spring 8 and the front case 2.1. To assemble the control subassembly 1.1, the shroud spring 8 is inserted into the needle shroud 7, and the needle shroud 7 with the shroud spring 8 is inserted into the front case 2.1. The cap 11 is arranged over the distal end of the needle shroud 7.

Figure 4:
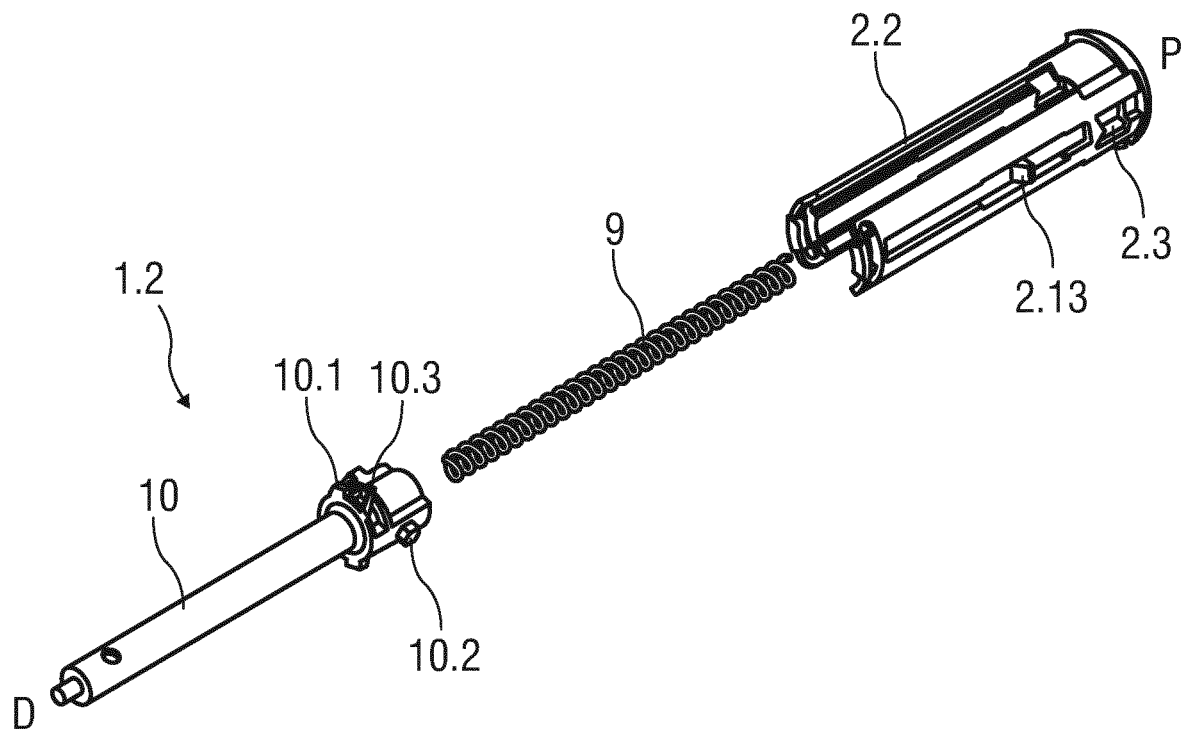
FIG. 4 is a perspective exploded view of an embodiment of a drive subassembly of an embodiment of a drug delivery device according to the present disclosure.

FIG. 4 is a perspective exploded view of an embodiment of a drive subassembly 1.2 of a drug delivery device 1 according to the present disclosure. In some embodiments, the drive subassembly 1.2 the plunger 10, the drive spring 9 and the rear case 2.2. Those of skill in the art will understand that if the viscosity or volume, for example, of the medicament M in the syringe 3 is changed, only parts of the drive subassembly 1.2 may need to be changed. To assemble the drive subassembly 1.2, the drive spring 9 is inserted into the plunger 10 and the plunger 10 is inserted in the rear case 2.2 in the proximal direction P thereby compressing the drive spring 9. Once the plunger 10 and the drive spring 9 30 reach a compressed position it is rotated by an angle, e.g. approximately 30° relative to the rear case 2.2, to engage the plunger 10 to the rear case 2.2. In some embodiments, the rear case 2.2 may have a cam surface to engage the plunger 10 to induce this rotation prior to the plunger 10 and the drive spring 9 reaching the compressed position.

Figure 5:
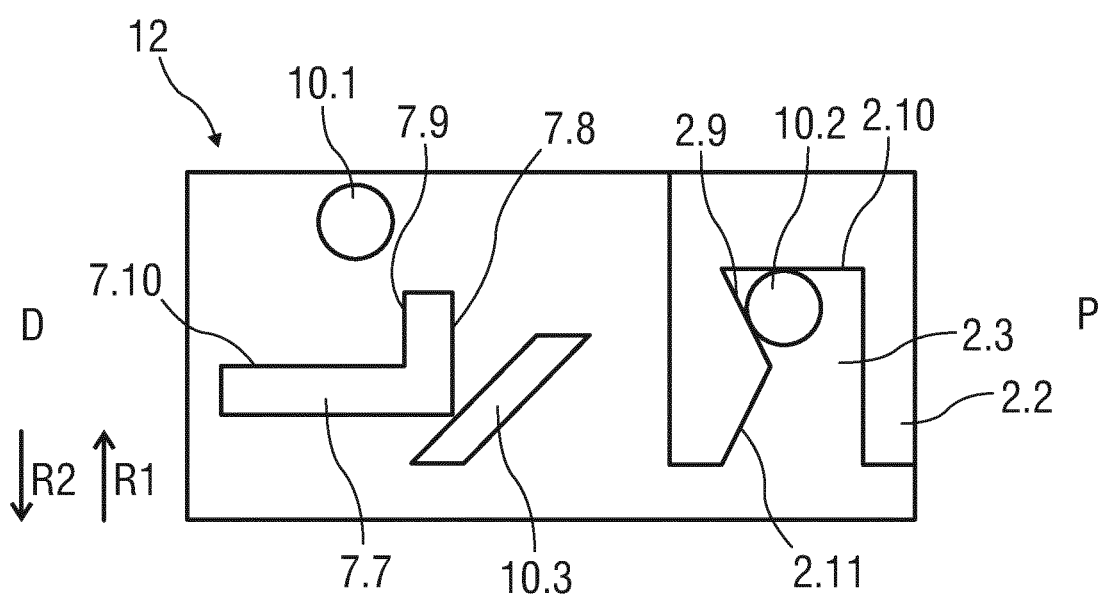
FIG. 5 is a schematic view of an embodiment of a plunger release mechanism of an embodiment of a drug delivery device according to the present disclosure.

FIG. 5 is a schematic view of an embodiment of a plunger release mechanism 12 of the drug delivery device 1 according to the present disclosure during assembly. The plunger release mechanism 12 is arranged for preventing release of the plunger 10 prior to retraction of the needle shroud 7 relative to the case 2 and for releasing the plunger 10 once the needle shroud 7 is sufficiently retracted. In some embodiments, the plunger release mechanism 12 comprises the plunger 10, the rear case 2.2, and the needle shroud 7 interacting with each other. In some embodiments, the needle shroud 7 is limited to axial movement relative to the case 2, and the plunger 10 can translate axially and rotate relative to the case 2.

In some embodiments, the plunger 10 comprises a first plunger boss 10.2 adapted to engage a case slot 2.3 in the case 2, a second plunger boss 10.1 adapted to engage a shroud rib 7.7 on the needle shroud 7, and a plunger rib 10.3 adapted to engage the shroud rib 7.7 on the needle shroud 7. In some embodiments, the shroud rib 7.7 comprises a proximal face 7.8 adapted to engage the plunger rib 10.3, and a distal face 7.9 and a longitudinal face 7.10 adapted to engage the second plunger boss 10.1. In some embodiments, the case slot 2.3 comprises a first angled surface 2.9 adapted to apply a rotational force in a first rotational direction R1 to the first plunger boss 10.2, a wall 2.10 adapted to abut the first plunger boss 10.2 to limit rotation of the plunger 10 relative to the case 2 in the first rotational direction R1, and a second angled surface 2.11 adapted to apply a rotational force in a second rotational direction R2, opposite the first rotational direction R1, to the first plunger boss 10.2.

In some embodiments of an assembly process of the drive subassembly 1.2, the plunger 10 with the drive spring 9 is inserted into the rear case 2.2. When the first plunger boss 10.2 is axially aligned with the case slot 2.3, the plunger 10 is rotated in the first rotational direction R1 until the first plunger boss 10.2 is moved into the case slot 2.3 until it abuts the wall 2.10. In this position, the first angled surface 2.9 prevents the first plunger boss 10.2 from moving in the second rotational direction R2, and thus prevents the plunger 10 from rotating relative to the case 2.

Figure 6:
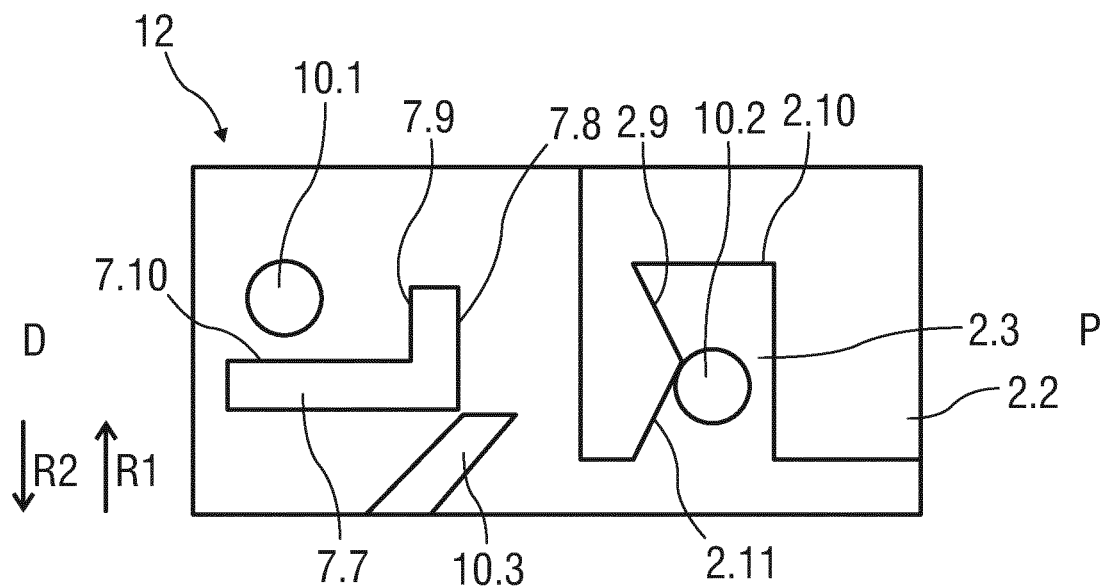
FIG. 6 is a schematic view of an embodiment of a plunger release mechanism of an embodiment of a drug delivery device according to the present disclosure during assembly.

After a syringe 3 (with the protective needle sheath 5 disposed on the needle 4) is inserted into the control assembly 1.1, the drive subassembly 1.2 is coupled to the control subassembly 1.1. In some embodiments, a pair of resilient beams 2.13 (shown in FIG. 1B) on the rear case 2.2 is adapted to snap into recesses 2.14 (shown in FIG. 3) in the front case 2.1 to lock the drive subassembly 1.2 to the control subassembly 1.1. As the drive assembly 1.2 is coupled to the control subassembly 1.1, the needle shroud 7 translates proximally (e.g., by use of an assembly jig) causing the shroud rib 7.7 to abut the plunger rib 10.3. As shown in FIG. 6, as the shroud rib 7.7 pushes plunger rib 10.3, the angle of the plunger rib 10.3 causes the plunger 10 to rotate relative to the case 2 in the second rotational direction R2, and the first plunger boss 10.2 rides along the first angled surface 2.9 onto the second angled surface 2.11. When the first plunger boss 10.2 is disposed on the second angled surface 2.11, the force of the drive spring 9 imparts a rotational force on the plunger 10 in the second rotational direction R2 due to the angle of the second angled surface 2.11.

Figure 7:
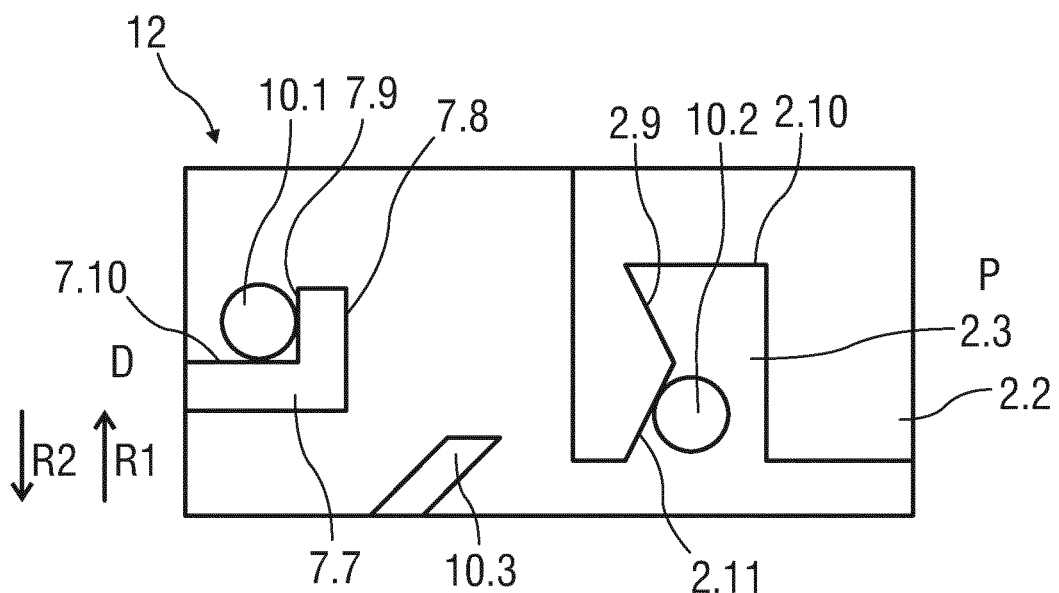
FIG. 7 is a schematic view of an embodiment of a plunger release mechanism of an embodiment of a drug delivery device according to the present disclosure after assembly.

As shown in FIG. 7, when the needle shroud 7 is released (e.g., by removing the assembly jig), the needle shroud 7 translates in the distal direction D relative to the case 2 under the force of the shroud spring 8 until the shroud rib 7.7 abuts the second plunger boss 10.1. For example, the distal face 7.9 of the shroud rib 7.7 may abut the second plunger boss 10.1 and maintain the needle shroud 7 in an axial position relative to the case 2. The first plunger boss 10.2 is prevented from disengaging the case slot 2.3, because the shroud rib 7.7 prevents the plunger 10 from rotating in the second rotational direction R2 relative to the case 2. For example, the longitudinal face 7.10 of the shroud rib 7.7 abuts the second plunger boss 10.1 to prevent rotation of the plunger 10.

Figure 8A:
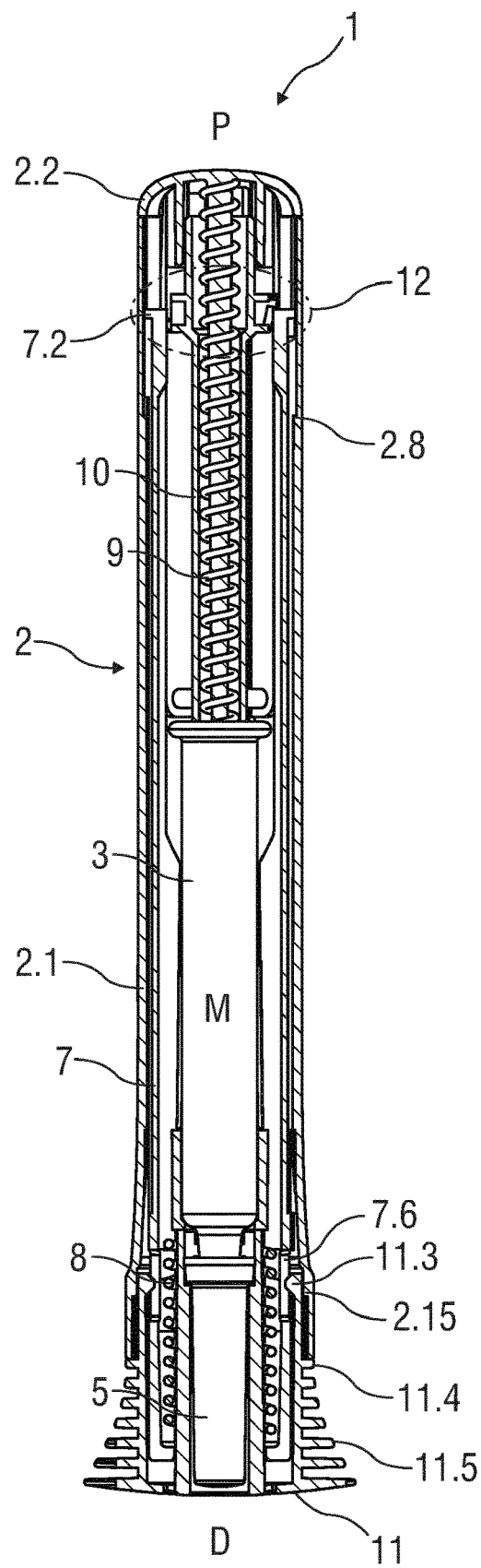
FIG. 8A is a longitudinal section of an embodiment of a drug delivery device according to the present disclosure after assembly.
Figure 8B:
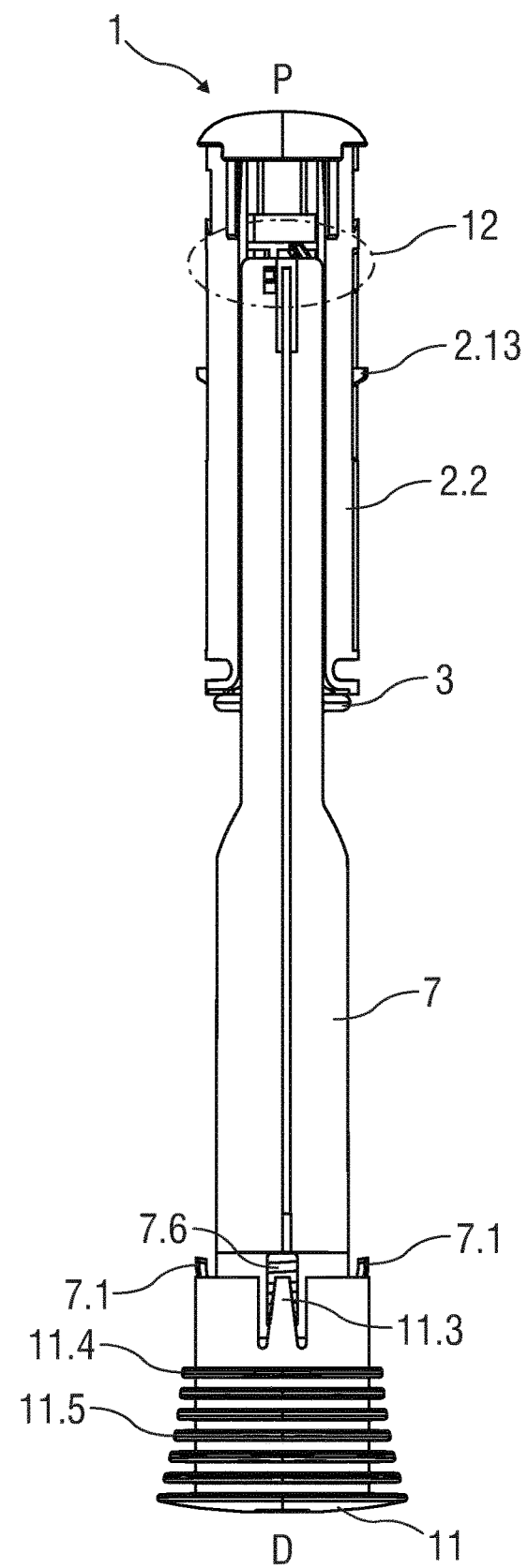
FIG. 8B is a schematic side view of an embodiment of a drug delivery device according to the present disclosure after assembly.

FIG. 8A is a longitudinal section of an embodiment of a drug delivery device 1 according to the present disclosure after final assembly, and FIG. 8B is a schematic side view of an embodiment of an drug delivery device 1 according to the present disclosure after final assembly, wherein the case 2 is removed for clarity.

In some embodiments, after the final assembly of the drive subassembly 1.2 to the control subassembly 1.1, the drug delivery device 1 may be kept in temperature controlled environment (e.g., cold chain storage) to, for example, reduce creep in highly stressed components, e.g. under load from the drive spring 9.

An exemplary sequence of operation of an embodiment of the drug delivery device 1 is as follows:

If applicable, the drug delivery device 1 is removed from the packaging. The medicament in the syringe 3 may be visually inspected through a viewing window (not shown), which can be a transparent part of the case 2 or a cut-out in the case 2 aligned with the syringe 3.

The cap 11 is removed by pulling it in the distal direction D away from the case 2. As the cap 11 translates distally relative to the case 2, the cap 11 engages the protective needle sheath 5 and pulls it off the needle 4 as the cap 11 is pulled in the distal direction D, and the compliant beam 11.3 disengages the aperture 7.6 in the needle shroud 7. The compliant beam 11.3 translates distally within the aperture 7.6 until it is no longer abutted radially by the radial stop 2.15 and engages a proximal surface of the aperture 7.6 (which may be ramped) and deflects radially to disengage the aperture 7.6. The syringe 3 is fixed in position relative to the case 2, so pulling the cap 11 in the distal direction D does not cause any axial movement of the syringe 3. In an exemplary embodiment, the syringe 3 is also fixed rotationally relative to the case 2 (e.g., by an interference fit with the case 2 and/or the needle shroud 7).

Figure 9A:
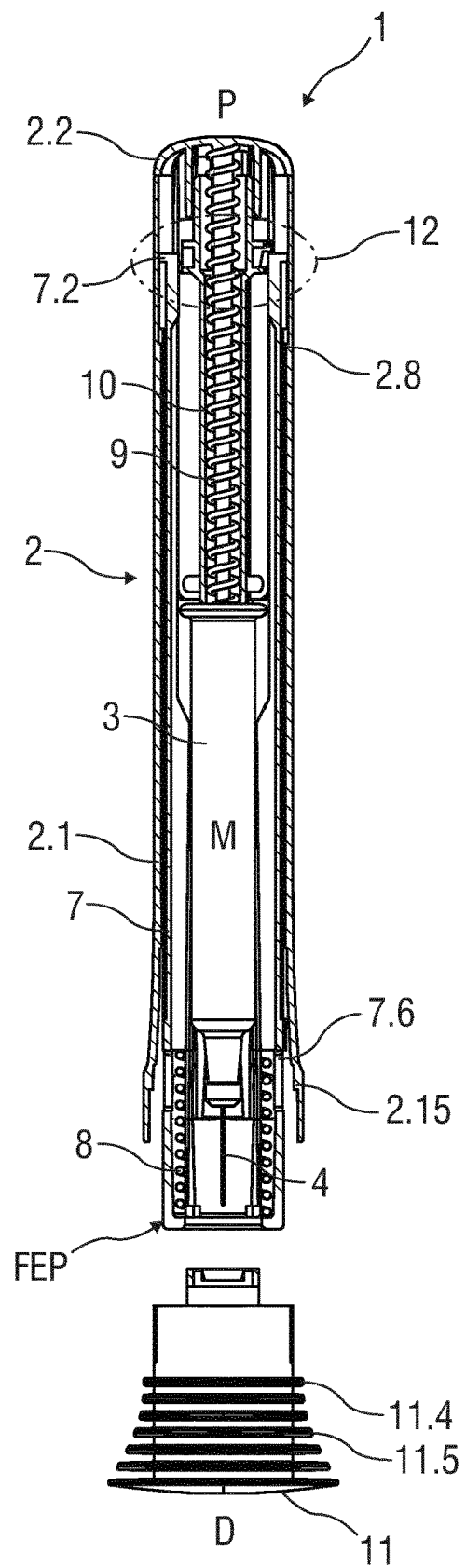
FIG. 9A is a longitudinal section of an embodiment of a shroud lock mechanism of an embodiment of a drug delivery device according to the present disclosure prior to use.
Figure 9B:
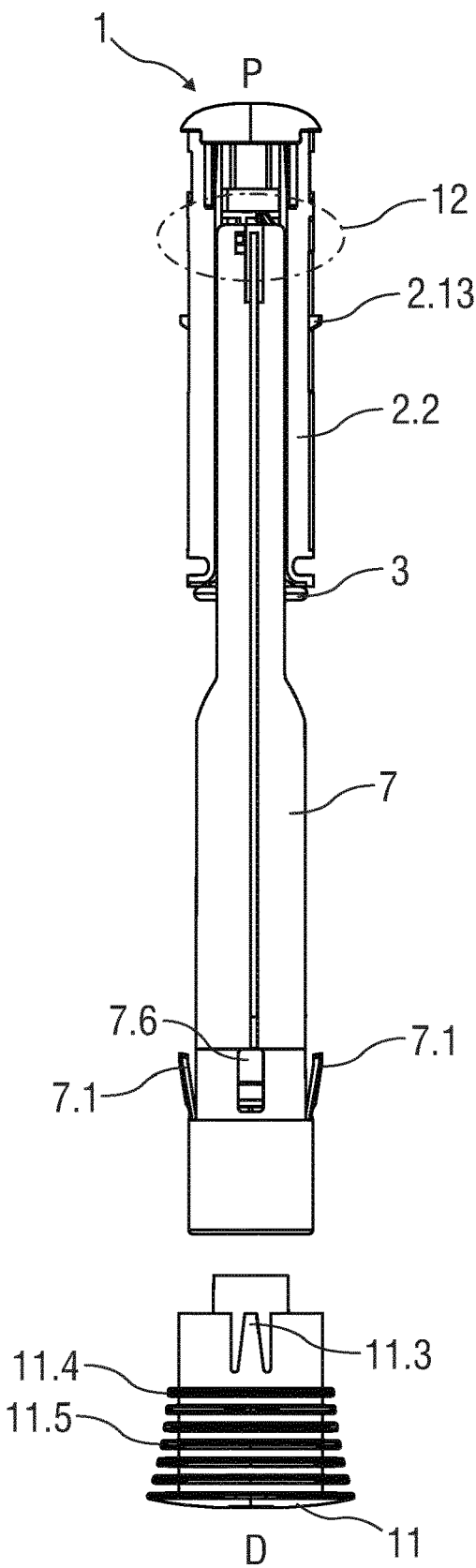
FIG. 9B is a schematic side view of an embodiment of a shroud lock mechanism of an embodiment of a drug delivery device according to the present disclosure prior to use.

FIG. 9A is a longitudinal section of an embodiment of the drug delivery device 1 according to the present disclosure prior to use. FIG. 9B is a schematic side view of an embodiment of the drug delivery device 1 according to the present disclosure prior to use, wherein the case 2 is removed for clarity.

When the cap 11 is removed, the needle shroud 7 is in a first extended position FEP relative to the case 2, protruding from the case 2 in the distal direction D. The first extended position FEP is defined by the second plunger boss 10.1 abutting the shroud rib 7.7.

Figure 10A:
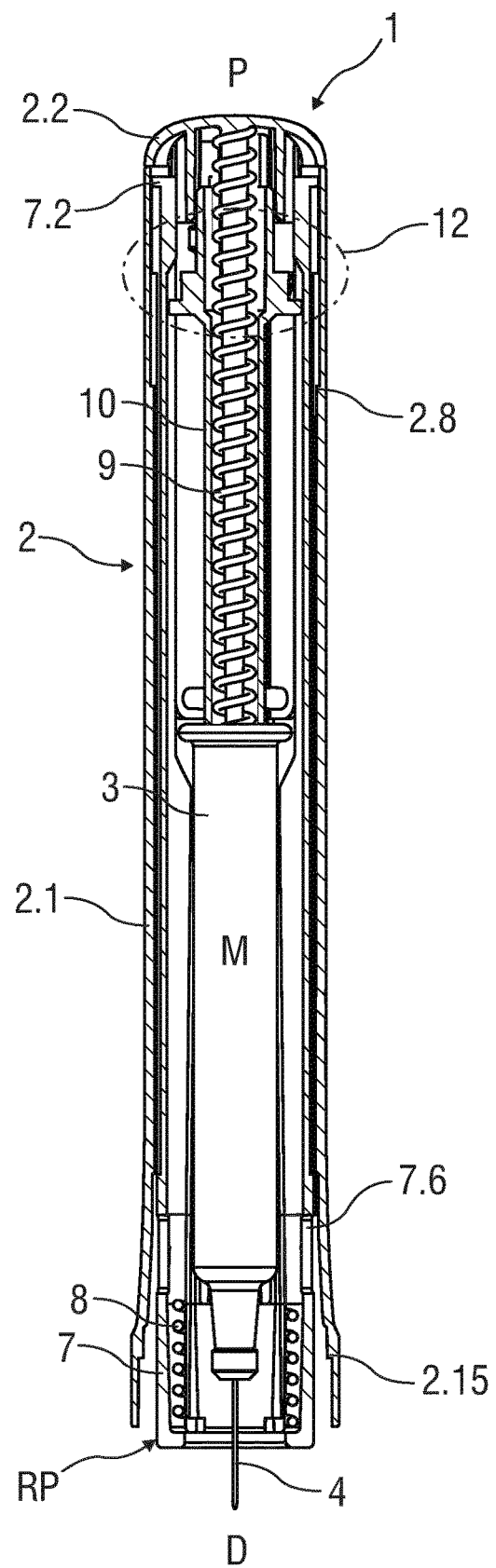
FIG. 10A is a longitudinal section of an embodiment of a drug delivery device according to the present disclosure during use.
Figure 10B:
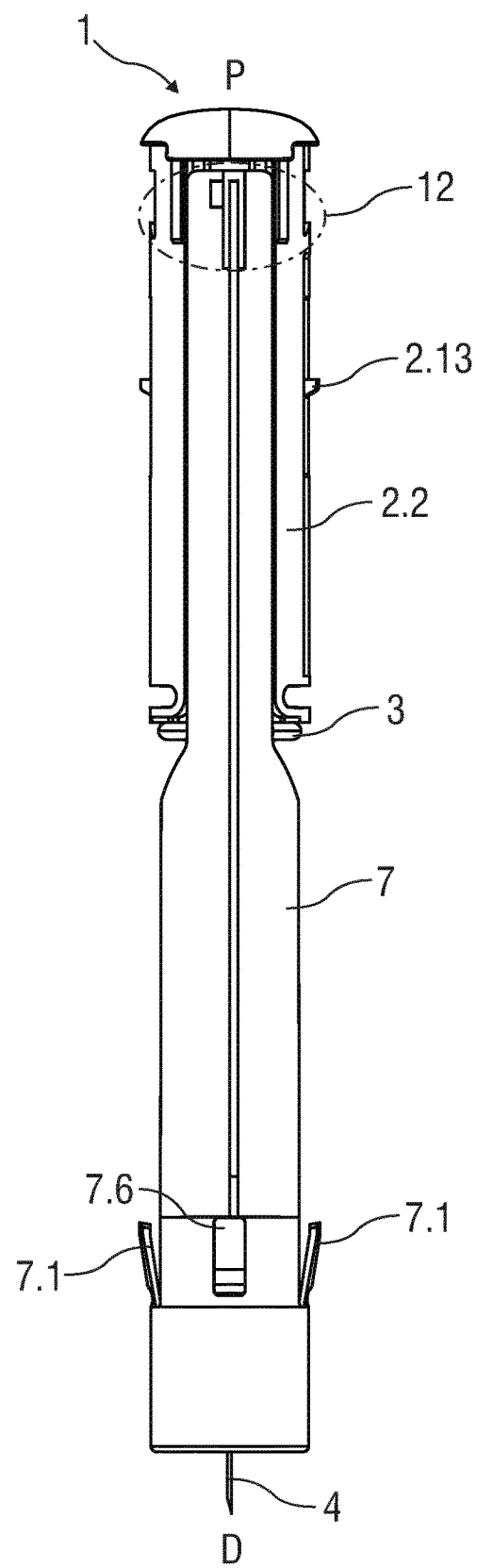
FIG. 10B is a schematic side view of an embodiment of a drug delivery device according to the present disclosure during use.

FIG. 10A is a longitudinal section of an embodiment of the drug delivery device 1 according to the present disclosure during use. FIG. 10B is a schematic side view of an embodiment of the drug delivery device 1 according to the present disclosure during use, wherein the case 2 is removed for clarity.

When the drug delivery device 1 is pressed against an injection site, the needle shroud 7 translates proximally relative to the case 2 against the biasing force of the shroud spring 8 from the first extended position FEP to a retracted position RP, as shown in FIGS. 10A and 10B.

Figure 11:
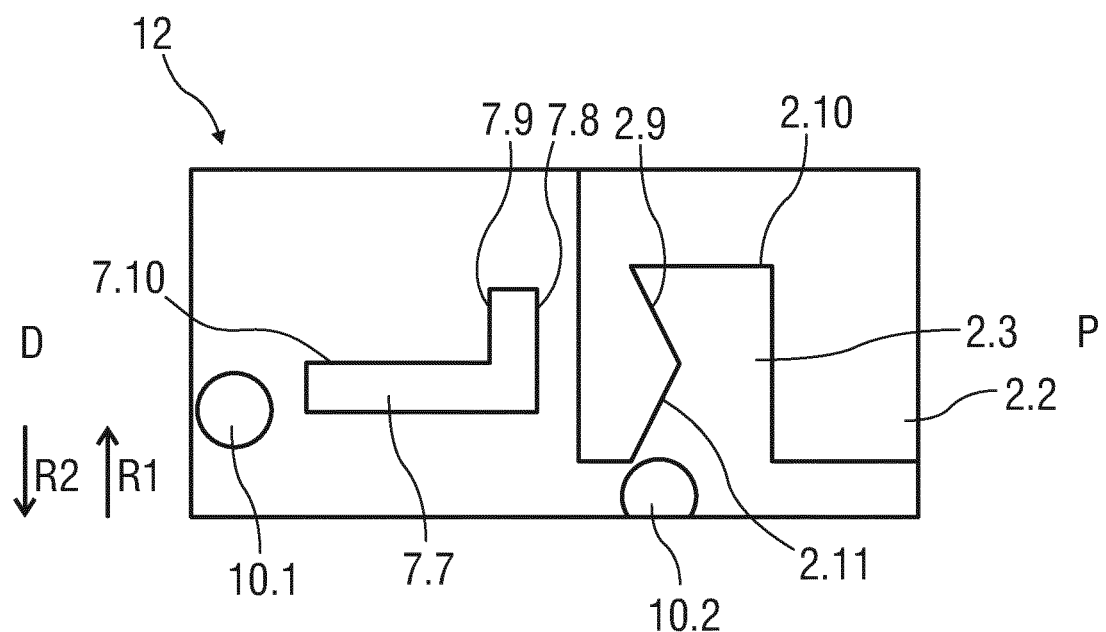
FIG. 11 is a schematic view of an embodiment of a plunger release mechanism of an embodiment of a drug delivery device according to the present disclosure during use.

FIG. 11 shows an embodiment of the plunger release mechanism 12 when the needle shroud 7 is in the retracted position RP. As the needle shroud 7 translates from the first extended position FEP to the retracted position RP, the needle shroud 7 translates distally causing the second plunger boss 10.1 to, starting from the position shown in FIG. 8, ride along the shroud rib 7.7 until it is distal of the shroud rib 7.7. When the second plunger boss 10.1 is distal of the shroud rib 7.7, the plunger 10 is no longer prevented from rotating in the second rotational direction R2 relative to the case 2. Thus, the force of the drive spring 9 on the plunger 10 and the engagement of the first plunger boss 10.2 on the second angled surface 2.11 in the case slot 2.3, causes the plunger 10 to rotate relative to the case 2. In an exemplary embodiment, the needle shroud 7 may include an aperture, a recess or a slot proximal of the shroud rib 7.7 to accommodate the second plunger boss 10.1 when the needle shroud 7 is in the retracted position RP and the plunger 10 rotates relative to the case 2.

In some embodiments, the shroud rib 7.7 (e.g., on the longitudinal face 7.10) may include a resistance feature (e.g., a projection, a ramp, a recess, etc.) adapted to abut the second plunger boss 10.1 as the needle shroud 7 translates from the first extended position FEP to the retracted position RP. When the second plunger boss 10.1 abuts the resistance feature, a tactile feedback is provided in the form of increased resistance to pressing the drug delivery device 1 against the injection site. The tactile feedback may be used to indicate that needle 4 will be inserted into the injection site upon further depression of the drug delivery device 1 against the injection site. Prior to the needle shroud 7 reaching the retracted position RP, if the drug delivery device 1 is removed from the injection site, the needle shroud and reposition as the needle shroud 7 will re-extend to its initial position under the force of the shroud spring 8. When the needle shroud 7 is in the retracted position RP, the needle 4 has been inserted into the injection site. Those of skill in the art will understand that a penetration depth of the needle 4 may be varied by, for example, limiting retraction of the needle shroud 7 relative to the case 2, modifying an axial position of the syringe 3 relative to the case 2, modifying a length of the needle 4, etc. Thus, the drug delivery device 1 of the present disclosure may be used for sub-cutaneous, intra-dermal and/or intra-muscular injection.

Figure 12A:
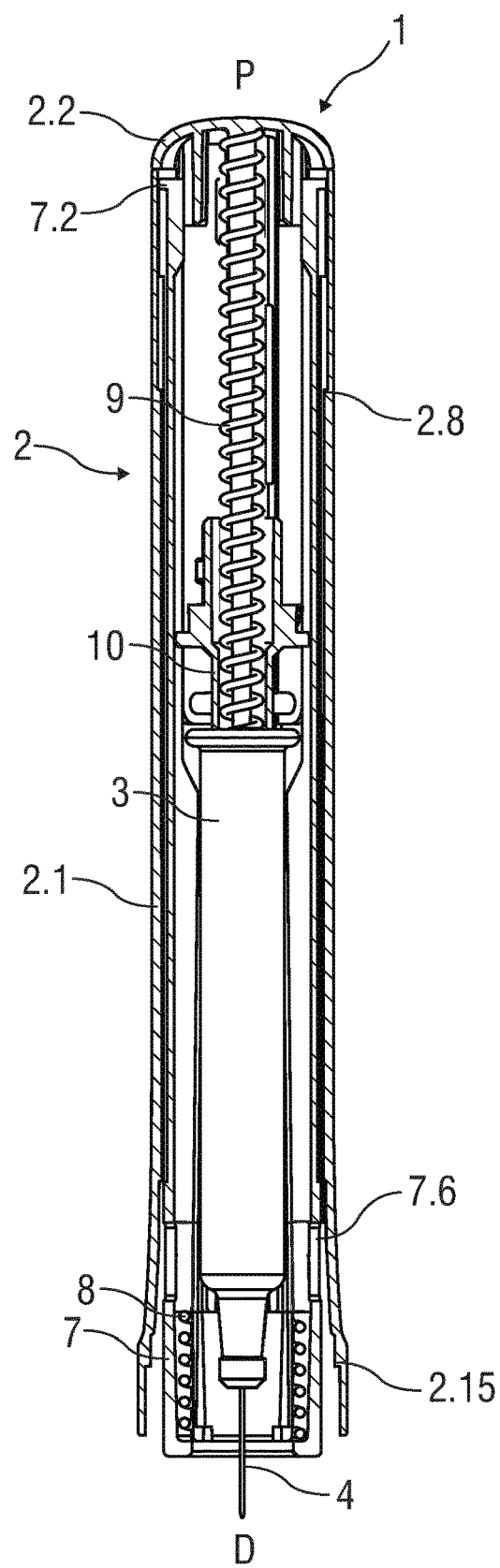
FIG. 12A is a longitudinal section of an embodiment of a drug delivery device according to the present disclosure during use.
Figure 12B:
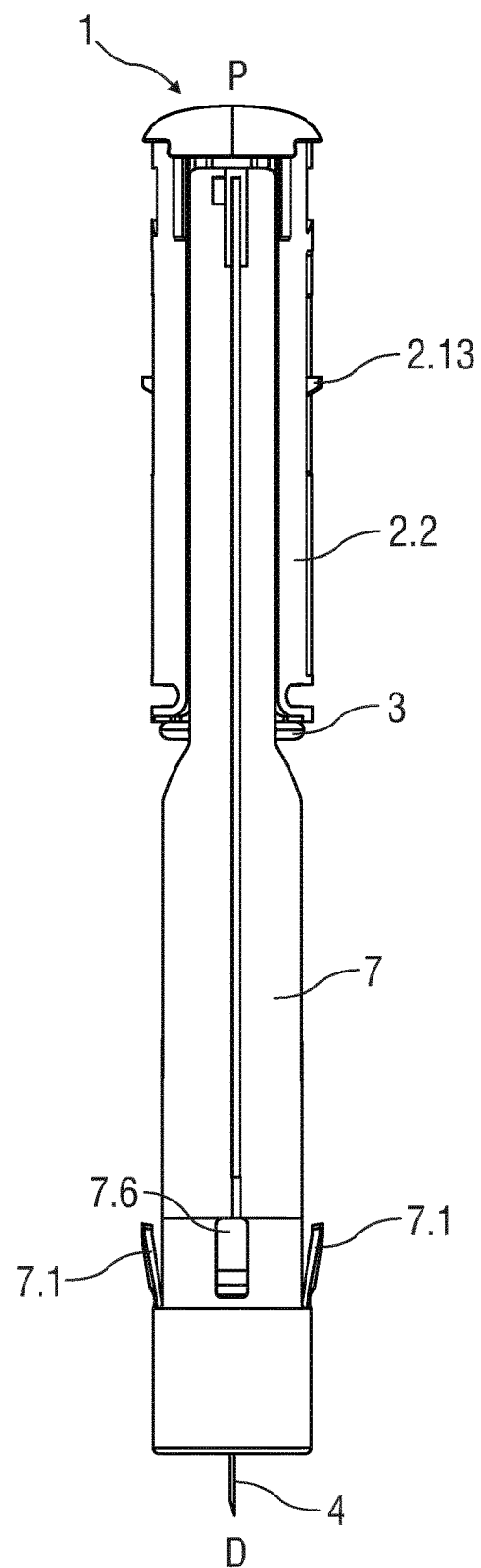
FIG. 12B is a schematic side view of an embodiment of a drug delivery device according to the present disclosure during use.

FIG. 12A is a longitudinal section of an embodiment of the drug delivery device 1 according to the present disclosure during use. FIG. 12B is a schematic side view of an embodiment of the drug delivery device 1 according to the present disclosure during use, wherein the case 2 is removed for clarity.

When the plunger 10 has rotated a sufficient distance in the second rotational direction R2 such that the first plunger boss 10.2 disengages the case slot 2.3, the plunger 10 is free to translate axially, under the force of the drive spring 9, relative to the case 2 to push the stopper 6 to deliver the medicament M from the syringe 3 through the needle 4.

In some embodiments, disengagement of the second plunger boss 10.1 from the shroud rib 7.7 and/or the first plunger boss 10.2 from the case slot 2.3 may provide an audible feedback indicating that delivery of the medicament M has started. A viewing window in the case 2 may allow for a visual feedback that the plunger 10 is advancing within the syringe 3 for assessing the progress of displacement of the medicament M.

Figure 13A:
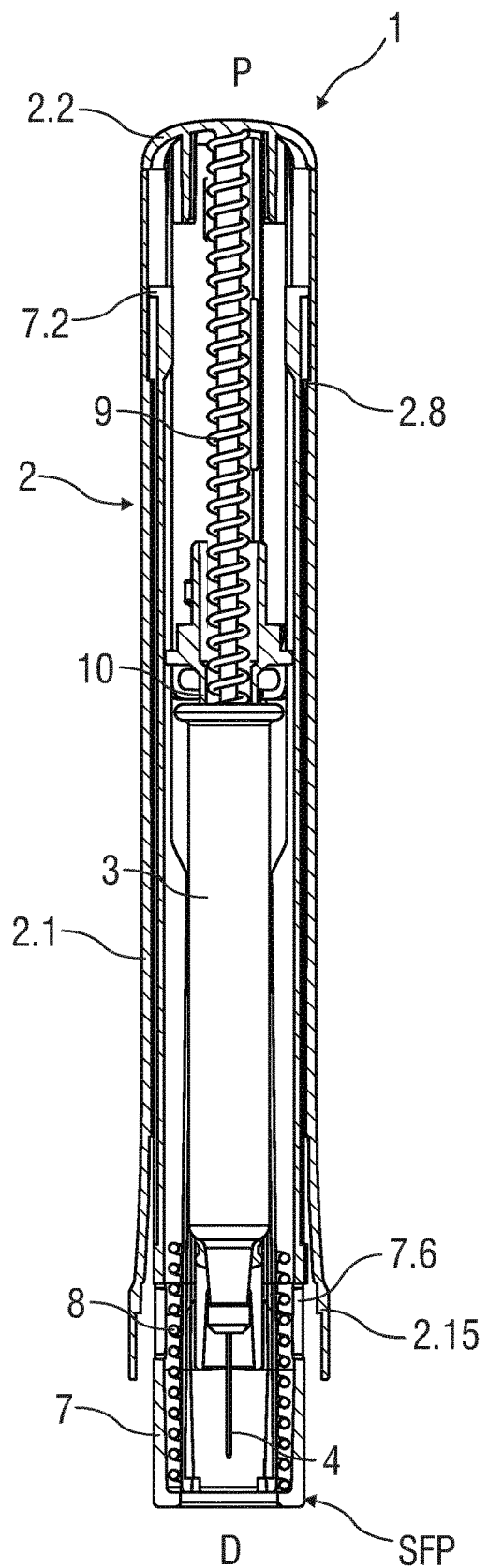
FIG. 13A is a longitudinal section of an embodiment of a drug delivery device according to the present disclosure after use.
Figure 13B:
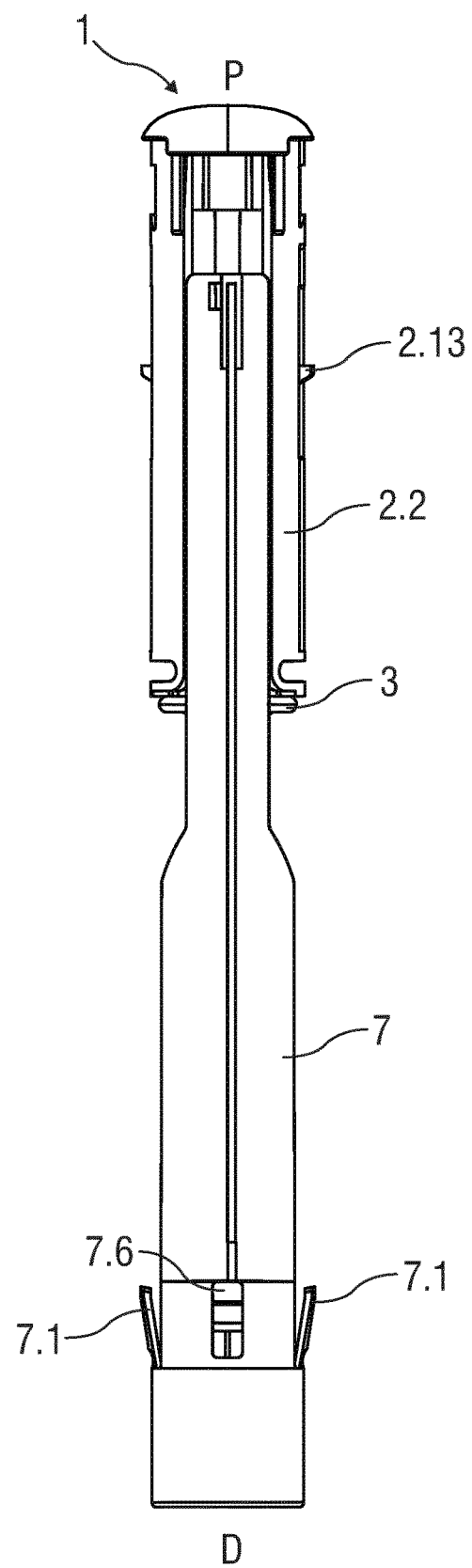
FIG. 13B is a schematic side view of an embodiment of a drug delivery device according to the present disclosure after use.

FIG. 13A is a longitudinal section of an embodiment of the drug delivery device 1 according to the present disclosure after use. FIG. 13B is a schematic side view of an embodiment of the drug delivery device 1 according to the present disclosure after use, wherein the case 2 is removed for clarity.

When the drug delivery device 1 is removed from the injection site, the needle shroud 7 translates distally relative to the case 2 from the retracted position RP to a second extended position SEP under the biasing force of the shroud spring 8. In the second extended position SEP, the needle shroud 7 extends beyond a distal tip of the needle 4 and locks in an axial position relative to the case 2. The second extended position SEP prevents needle-stick injury and may also indicate that the drug delivery device 1 has been used (because the needle shroud 7 cannot move proximally from the second extended position SEP). In some embodiments, in the second extended position SEP, the needle shroud 7 protrudes further, e.g. 2 mm, from the case 2 than in the first extended position FEP. The needle shroud 7 may include an indicia (e.g., a red ring, text, a graphic) on a portion which is visually accessible when the needle shroud 7 is in the second extended position SEP but not in the first extended position FEP. The indicia may indicate that the drug delivery device 1 has been used.

FIGS. 14A to 14E are schematic views of another embodiment of a plunger release mechanism 12 of the drug delivery device 1 according to the present disclosure. The plunger release mechanism 12 is arranged for preventing release of the plunger 10 prior to retraction of the needle shroud 7 relative to the case 2 and for releasing the plunger 10 once the needle shroud 7 is sufficiently retracted. In some embodiments, the plunger release mechanism 12 comprises the plunger 10, the rear case 2.2, and the needle shroud 7 interacting with each other. In an exemplary embodiment, the needle shroud 7 is limited to axial movement relative to the case 2, and the plunger 10 can translate axially and rotate relative to the case 2.

In some embodiments, the plunger 10 comprises a second plunger boss 10.1 adapted to engage a shroud rib 7.7 on the needle shroud 7 and a first plunger boss 10.2 adapted to engage a case slot 2.3 in the case 2, and a plunger rib 10.3 adapted to engage the shroud rib 7.7 on the needle shroud 7. In some embodiments, the shroud rib 7.7 comprises a proximal face 7.8 adapted to engage the plunger rib 10.3, and a distal face 7.9 adapted to engage the second plunger boss 10.1. In some embodiments, the case slot 2.3 comprises a first angled surface 2.9 adapted to apply a rotational force in a first rotational direction R1 to the first plunger boss 10.2, a wall 2.10 adapted to abut the first plunger boss 10.2 to limit rotation of the plunger 10 relative to the case 2 in the first rotational direction R1, and a transversal surface 2.16.

Figure 14A:
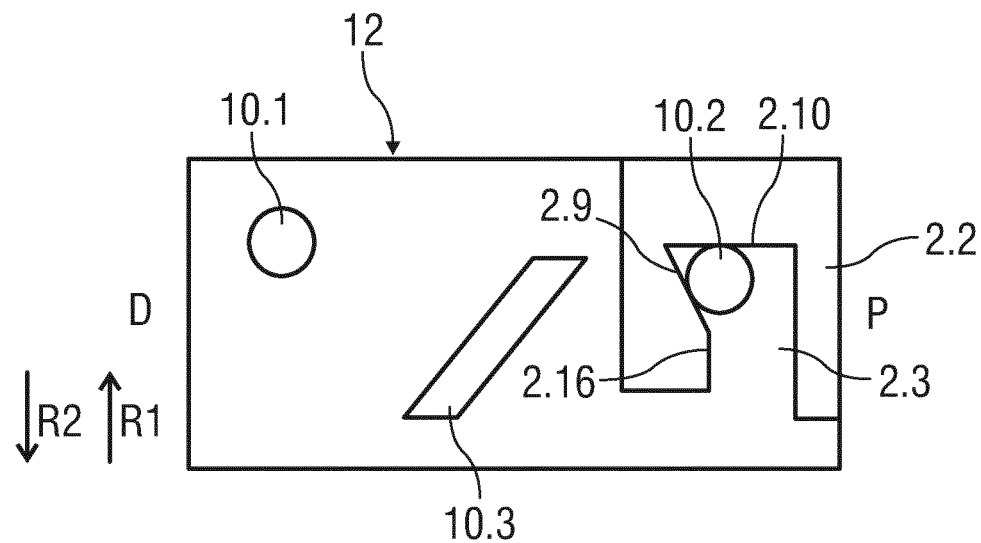
FIGS. 14A-E are schematic views of another embodiment of a plunger release mechanism before, during and after use.

FIG. 14A is a schematic view of an embodiment of the plunger release mechanism 12 of the drug delivery device 1 according to the present disclosure during assembly of the drive subassembly 1.2.

In some embodiments of an assembly process of the drive subassembly 1.2, the plunger 10 with the drive spring 9 is inserted into the rear case 2.2. When the first plunger boss 10.2 is axially aligned with the case slot 2.3, the plunger 10 is rotated in the first rotational direction R1 until the first plunger boss 10.2 is moved into the case slot 2.3 until it abuts the wall 2.10. In this position, the first angled surface 2.9 prevents the first plunger boss 10.2 from moving in the second rotational direction R2, and thus prevents the plunger 10 from rotating relative to the case 2.

Figure 14B:
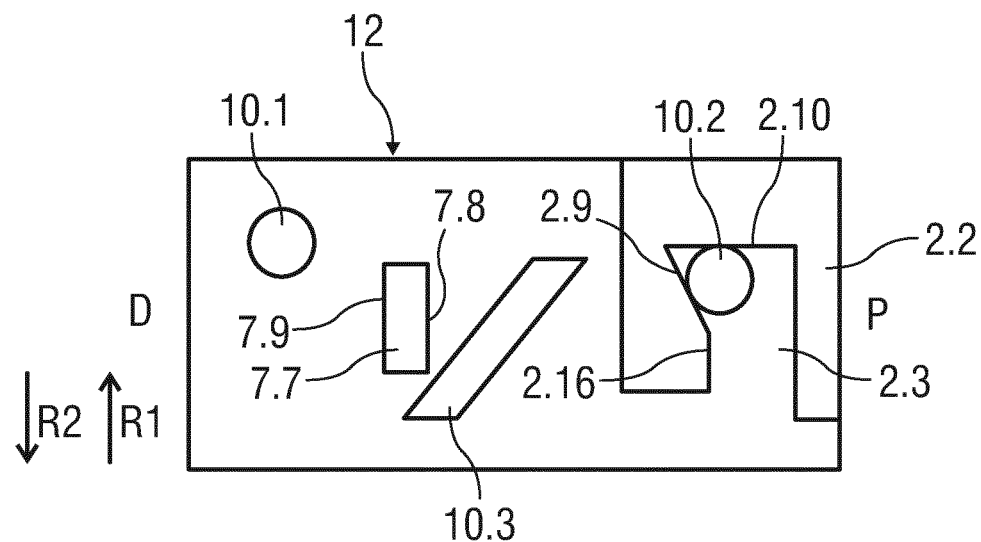
Figure 14C:
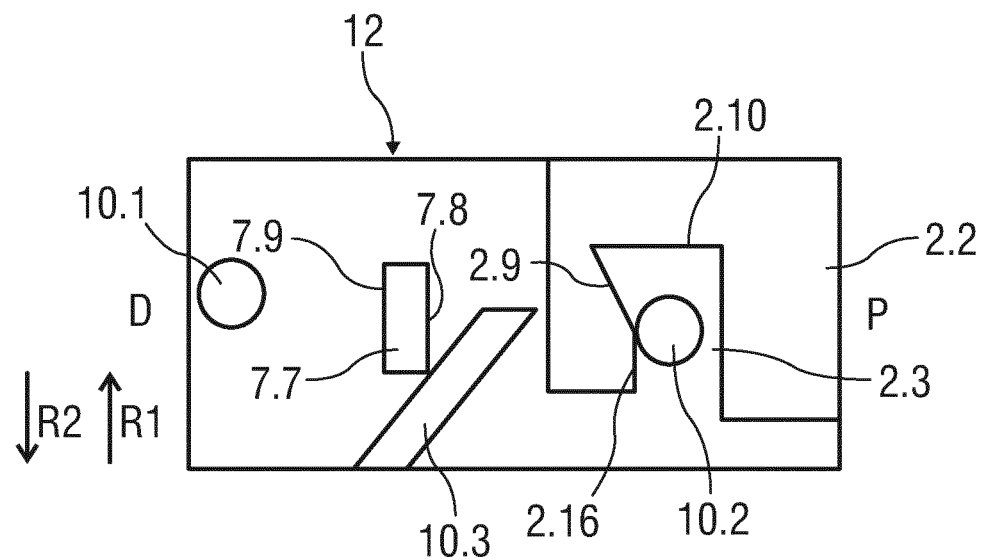

After a syringe 3 (with the protective needle sheath 5 disposed on the needle 4) is inserted into the control assembly 1.1, the drive subassembly 1.2 is coupled to the control subassembly 1.1. In some embodiments, a pair of resilient beams 2.13 (shown in FIG. 1B) on the rear case 2.2 is adapted to snap into recesses 2.14 (shown in FIG. 3) in the front case 2.1 to lock the drive subassembly 1.2 to the control subassembly 1.1. FIG. 14B shows the drive assembly 1.2 being coupled to the control subassembly 1.1, wherein the needle shroud 7 translates proximally (e.g., by use of an assembly jig) causing the shroud rib 7.7 to abut the plunger rib 10.3. As shown in FIG. 14C, as the shroud rib 7.7 pushes plunger rib 10.3, the angle of the plunger rib 10.3 causes the plunger 10 to rotate relative to the case 2 in the second rotational direction R2, and the first plunger boss 10.2 rides along the first angled surface 2.9 onto the transversal surface 2.16.

Figure 14D:
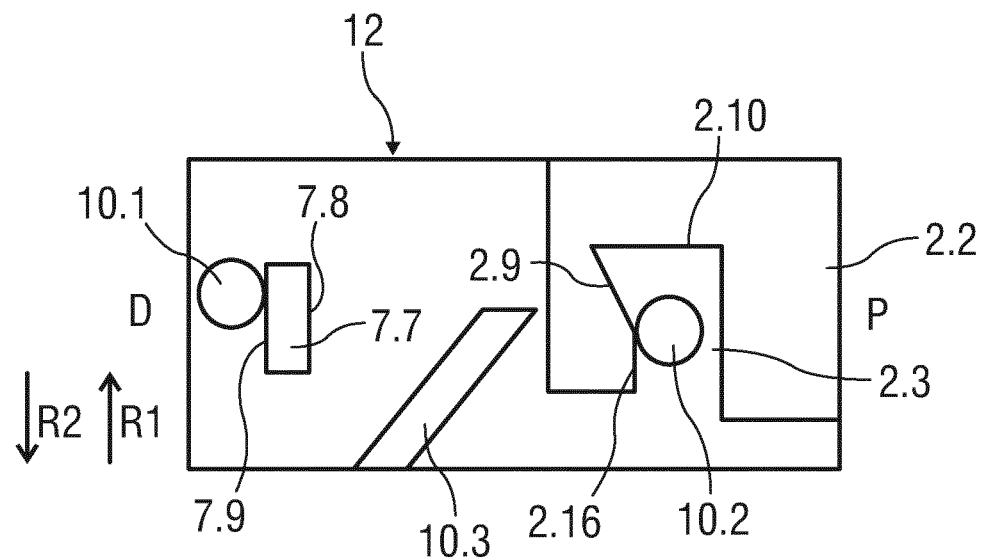

As shown in FIG. 14D, when the needle shroud 7 is released (e.g., by removing the assembly jig), the needle shroud 7 translates in the distal direction D relative to the case 2 under the force of the shroud spring 8 until the shroud rib 7.7 abuts the second plunger boss 10.1. For example, the distal face 7.9 of the shroud rib 7.7 may abut the second plunger boss 10.1 and maintain the needle shroud 7 in an axial position relative to the case 2. The first plunger boss 10.2 is prevented from disengaging the case slot 2.3 as it abuts the transversal surface 2.16 in the distal direction D.

Figure 14E:
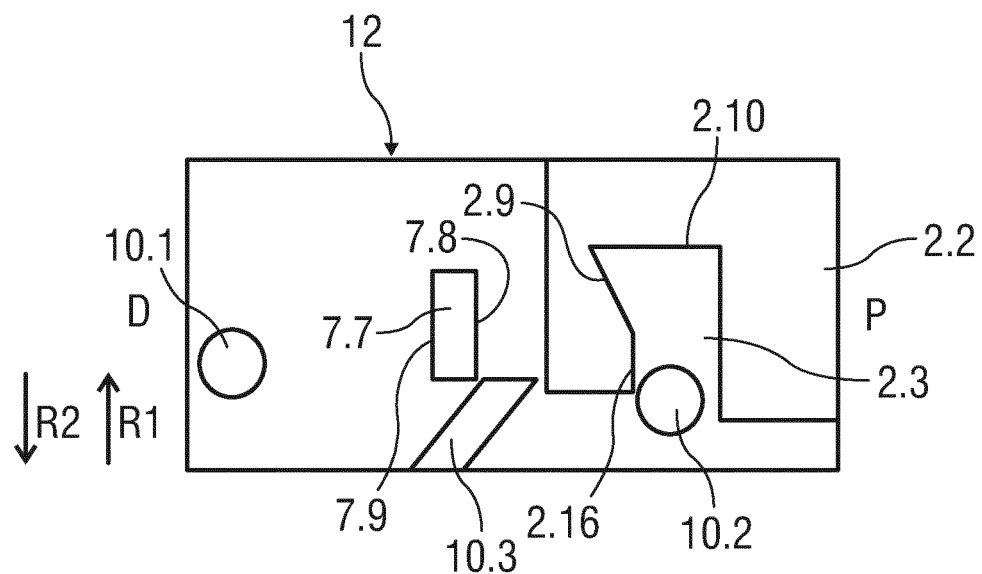

FIG. 14E shows an embodiment of the plunger release mechanism 12 when the needle shroud 7 is in the retracted position RP. As the needle shroud 7 translates from the first extended position FEP to the retracted position RP, the needle shroud 7 translates distally causing the shroud rib 7.7 to, starting from the position shown in FIG. 14D, ride along the plunger rib 10.3 thereby rotating the first plunger boss 10.2 in the second rotational direction R2 along the transversal surface 2.16 until the first plunger boss 10.2 disengages the case slot 2.3 thus releasing the plunger 10. Then, under the force of the drive spring 9, the plunger 10 translates axially relative to the case 2 to deliver the medicament M from the syringe 3. In some embodiments, a tactile feedback may be provided in the form of an increase in resistance when the needle shroud 7 abuts and pushes against the plunger rib 10.3. The tactile feedback may indicate that needle insertion is or will commence, or medicament delivery will be initiated, if the drug delivery device 1 is pressed further against the injection site.

In some embodiments, the transversal surface 2.16 could be replaced by or comprise a concave shape for preventing inadvertent release of the plunger 10.

In some embodiments, the plunger 10 may not have the second plunger boss 10.1, the plunger rib 10.3 may be disposed at different angle than as described above, and the case slot 2.3 may not be angled relative to a transverse axis of the case 2. In such embodiments, when the drug delivery device 1 is assembled, the plunger 10 is maintained in axial position relative to the case 2, because the first plunger boss 10.2 engages the case slot 2.3. However, the case slot 2.3 may not impart any rotational force on the first plunger boss 10.2 (or, in another embodiment, the case slot 2.3 may be angled to impart a rotational force on the first plunger boss 10.2 in the first rotational direction R1 to ensure that the first plunger boss 10.2 does not disengage the case slot 2.3 inadvertently).

In some embodiments, the syringe 3 used in the drug delivery device 1 may be a syringe capable of containing approximately 1 ml of the medicament M. In some embodiments, the syringe 3 used in the drug delivery device 1 may be a syringe capable of containing approximately 2 ml of the medicament M.

The drug delivery device 1 according to the present disclosure may have an increased shelf-life compared to conventional drug delivery devices, because, for example, only the plunger 10 is subjected to the relatively high force of the drive spring 9.

The drug delivery device 1 according to the present disclosure may be used as a platform as the drive spring 9 can be changed to alter a force applied to the plunger 10, e.g., for delivering medicaments with different viscosities drugs or reconstituted medicaments, or changing a time required to inject a dose of the medicament.

The cap 11 is suitable for being applied with any kind of injection device or drug delivery device.

Figure 15A:
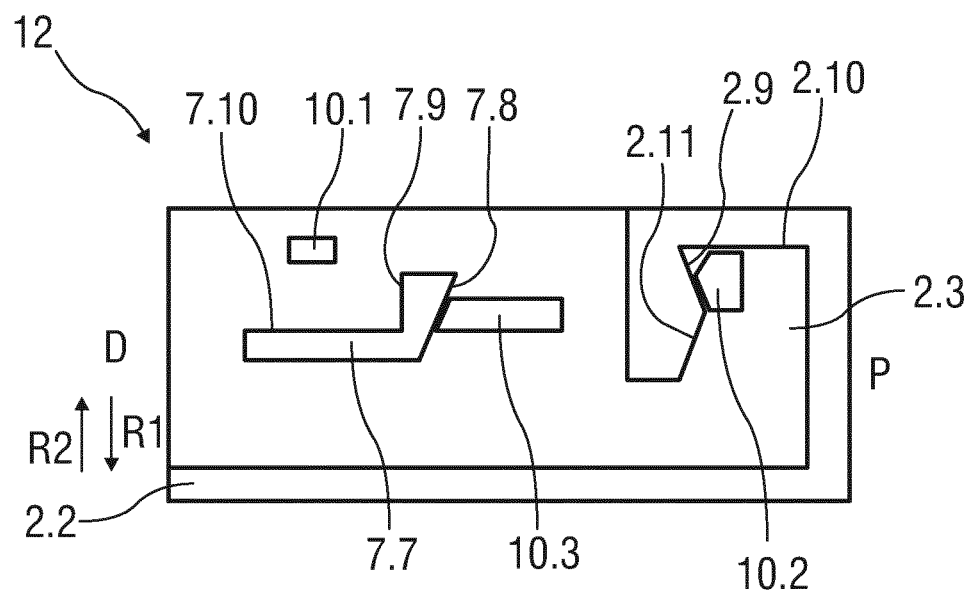
FIGS. 15A-D are schematic views of another embodiment of a plunger release mechanism before, during and after use.

FIG. 15A is a schematic view of another embodiment of a plunger release mechanism 12 of a drug delivery device during assembly.

The drug delivery device 1 may be the drug delivery device 1 as disclosed and illustrated herein. The plunger release mechanism shown in FIG. 15A may replace the plunger release mechanism shown in FIGS. 5, 6, 7 and 11 or the plunger release mechanism shown in FIGS. 14A to 14E.

The plunger release mechanism 12 shown in FIG. 15A is arranged for preventing release of the plunger 10 prior to retraction of the needle shroud 7 relative to the case 2 and for releasing the plunger 10 once the needle shroud 7 is sufficiently retracted. In some embodiments, the plunger release mechanism 12 comprises the plunger 10, the rear case 2.2, and the needle shroud 7 interacting with each other. In some embodiments, the needle shroud 7 is limited to axial movement relative to the case 2, and the plunger 10 can translate axially and rotate relative to the case 2.

In some embodiments, the plunger 10 comprises a second plunger boss 10.1 adapted to engage a shroud rib 7.7 on the needle shroud 7, a first plunger boss 10.2 adapted to engage a case slot 2.3 in the case 2, and a plunger rib 10.3 adapted to engage the shroud rib 7.7 on the needle shroud 7. In some embodiments, the shroud rib 7.7 comprises a proximal face 7.8 adapted to engage the plunger rib 10.3, and a distal face 7.9 and a longitudinal face 7.10 adapted to engage the second plunger boss 10.1. In some embodiments, the case slot 2.3 comprises a first angled surface 2.9 adapted to apply a rotational force in a first rotational direction R1 to the first plunger boss 10.2, a wall 2.10 adapted to abut the first plunger boss 10.2 to limit rotation of the plunger 10 relative to the case 2 in the first rotational direction R1, and a second angled surface 2.11 adapted to apply a rotational force in a second rotational direction R2, opposite the first rotational direction R1, to the first plunger boss 10.2.

One or both of the proximal face 7.8 and the plunger rib 10.3 may be angled such that, when the proximal face 7.8 and the plunger rib 10.3 axially abut each other, an axial force applied to the shroud rib 7.7 in the proximal direction P and/or to the plunger 10 in the distal direction D generates a torque for rotating the plunger 10 in the second rotational direction R2.

In some embodiments of an assembly process of the drive subassembly 1.2, the plunger 10 with the drive spring 9 is inserted into the rear case 2.2. When the first plunger boss 10.2 is axially aligned with the case slot 2.3, the plunger 10 is rotated in the first rotational direction R1 until the first plunger boss 10.2 is moved into the case slot 2.3 until it abuts the wall 2.10. In this position, the first angled surface 2.9 prevents the first plunger boss 10.2 from moving in the second rotational direction R2, and thus prevents the plunger 10 from rotating relative to the case 2.

Figure 15B:
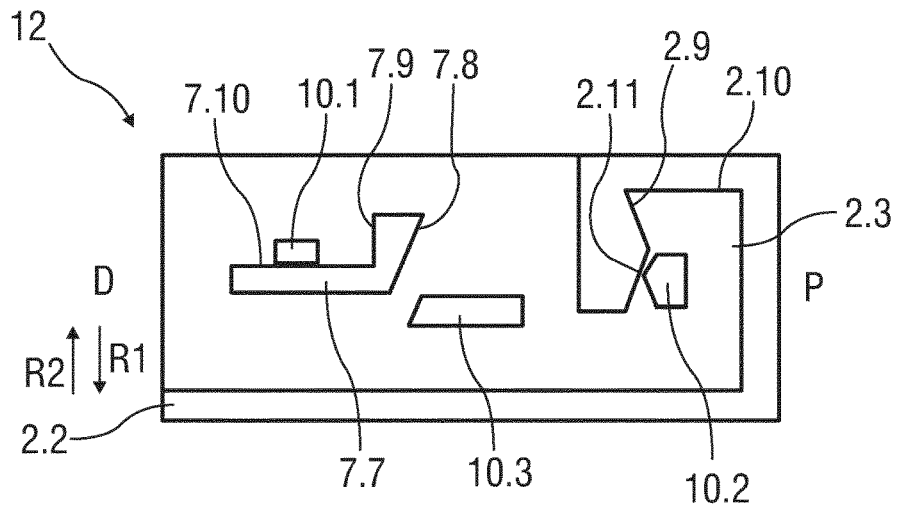

After a syringe 3 (with the protective needle sheath 5 disposed on the needle 4) is inserted into the control subassembly 1.1, the drive subassembly 1.2 is coupled to the control subassembly 1.1. In some embodiments, a pair of resilient beams 2.13 (shown in FIG. 1B) on the rear case 2.2 is adapted to snap into recesses 2.14 (shown in FIG. 3) in the front case 2.1 to lock the drive subassembly 1.2 to the control subassembly 1.1. As the drive subassembly 1.2 is coupled to the control subassembly 1.1, the needle shroud 7 translates proximally (e.g., by use of an assembly jig or without an assembly jig) causing the shroud rib 7.7 to abut the plunger rib 10.3. As shown in FIG. 15B, as the shroud rib 7.7 pushes the plunger rib 10.3, the angle of the plunger rib 10.3 and/or the angle of the proximal face 7.8 cause/causes the plunger 10 to rotate relative to the case 2 in the second rotational direction R2, and the first plunger boss 10.2 rides along the first angled surface 2.9 onto the second angled surface 2.11. When the first plunger boss 10.2 is disposed on the second angled surface 2.11, the force of the drive spring 9 imparts a rotational force on the plunger 10 in the second rotational direction R2 due to the angle of the second angled surface 2.11.

Figure 15C:
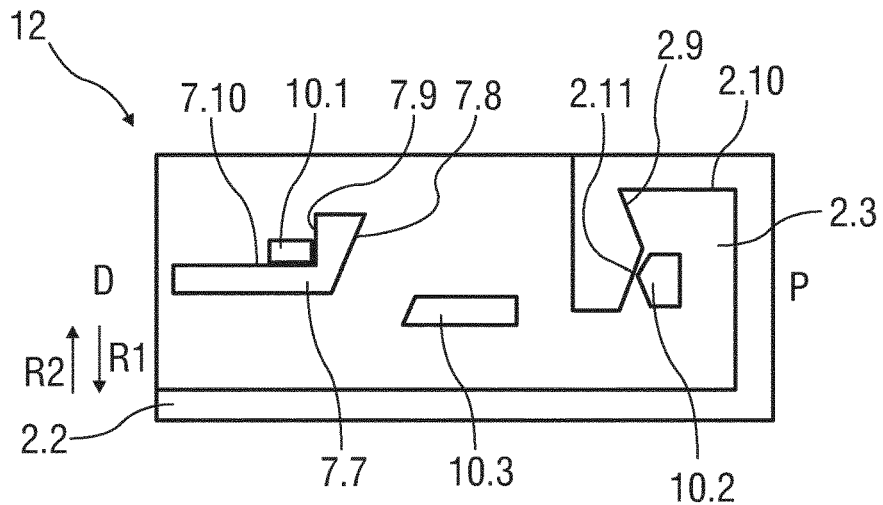

As shown in FIG. 15C, when the needle shroud 7 is released (e.g., by removing the assembly jig), the needle shroud 7 translates in the distal direction D relative to the case 2 under the force of the shroud spring 8 until the shroud rib 7.7 abuts the second plunger boss 10.1. For example, the distal face 7.9 of the shroud rib 7.7 may abut the second plunger boss 10.1 and maintain the needle shroud 7 in an axial position relative to the case 2. The first plunger boss 10.2 is prevented from disengaging the case slot 2.3, because the shroud rib 7.7 prevents the plunger 10 from rotating in the second rotational direction R2 relative to the case 2. For example, the longitudinal face 7.10 of the shroud rib 7.7 abuts the second plunger boss 10.1 to prevent rotation of the plunger 10.

Figure 15D:
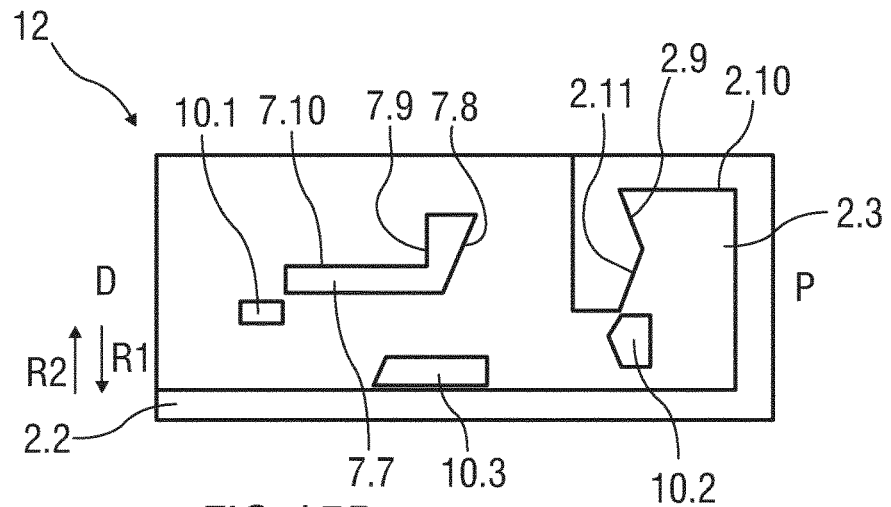

FIG. 15D shows the plunger release mechanism 12 when the needle shroud 7 is in the retracted position RP. As the needle shroud 7 translates from the first extended position FEP to the retracted position RP, the needle shroud 7 translates in the distal direction D causing the second plunger boss 10.1 to, starting from the position shown in FIG. 3, ride along the shroud 30 rib 7.7 until it is distal of the shroud rib 7.7. When the second plunger boss 10.1 is distal of the shroud rib 7.7, the plunger 10 is no longer prevented from rotating in the second rotational direction R2 relative to the case 2. Thus, the force of the drive spring 9 on the plunger 10 and the engagement of the first plunger boss 10.2 on the second angled surface 2.11 in the case slot 2.3, causes the plunger 10 to rotate relative to the case 2 in the second rotational direction R2.

When the plunger 10 has rotated a sufficient distance in the second rotational direction R2 such that the first plunger boss 10.2 disengages the case slot 2.3, the plunger 10 is free to translate axially in the distal direction D, under the force of the drive spring 9, relative to the case 2 to push the stopper 6 to deliver the medicament M from the syringe 3 through the needle 4.

In some embodiments, disengagement of the second plunger boss 10.1 from the shroud rib 7.7 and/or the first plunger boss 10.2 from the case slot 2.3 may provide an audible feedback indicating that delivery of the medicament M has started.

In some embodiments, the rotation of the plunger 10 in the second rotational direction R2 is limited by a part of the plunger 10, e.g. at least one of the second plunger boss 10.1, the first plunger boss 10.2 and the plunger rib 10.3 abutting a surface of the case 2, e.g. the front case 2.1 or the rear case 2.2. In the embodiment shown in FIG. 15D, the rotation of the plunger 10 in the second rotational direction R2 is limited by the plunger rib 10.3 abutting a surface of the rear case 2.2.

This abutment of the plunger 10 on the case 2 may generate an audible and/or tactile feedback indicating that the plunger 10 is being released.

The occurrence and loudness of this feedback may depend on the materials of the plunger 10 and case 2, a rotational speed of the plunger 10 and an extent of the part of the plunger 10, e.g. the plunger rib 10.3, impacting on the case 2. The rotational speed depends on friction between the case 2, e.g. the second angled surface 2.11, and the plunger 10, e.g. the first plunger boss 10.2, on the plunger's 10 moment of inertia, the force of the drive spring 9 and the angle of the second angled surface 2.11.

In some embodiments, it may be preferred to avoid or mitigate this audible feedback.

Figure 16A:
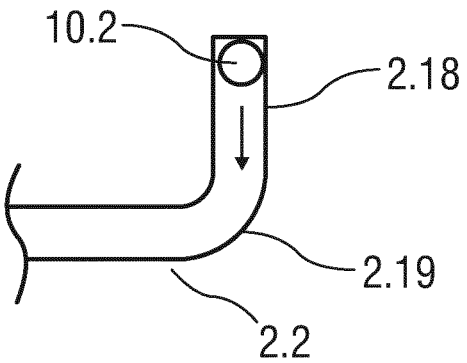
FIGS. 16A-C are schematic views of an embodiment of a guide curve.
Figure 16B:
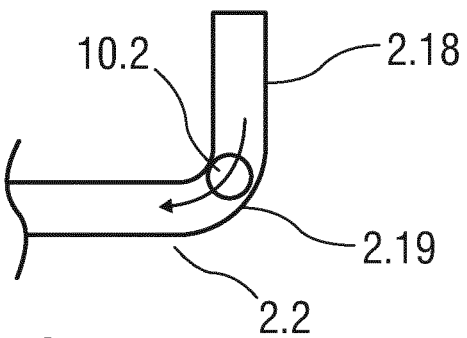
Figure 16C:
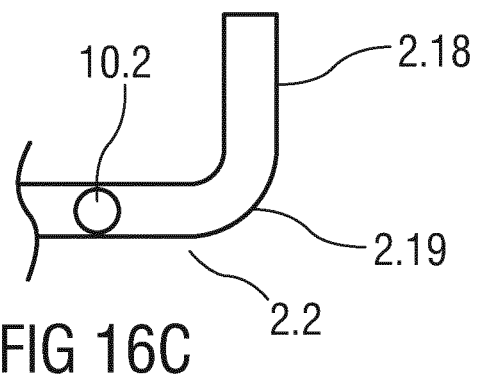

This may be achieved by guiding the movement of the plunger 10 during release of the first plunger boss 10.2 from the case slot 2.3 as schematically illustrated in FIGS. 16A to 16C. For this purpose, a guide curve 2.18 may be arranged in the case 2, e.g. in the rear case 2.2, the guide curve 2.18 engaging a part of the plunger, e.g. at least one of the first plunger boss 10.2, the first plunger boss 10.2 and the plunger rib 10.3. In FIGS. 16A to 16C, said part of the plunger 10 is shown to have a circular cross section. Those skilled in the art will understand that said part may likewise have a different shape, e.g. the shape of one of the first plunger boss 10.2, the first plunger boss 10.2 and the plunger rib 10.3 as shown in FIGS. 15A to 15D or in one of the FIGS. 5, 6, 7, 11, 14A to 14E. Likewise, one of the first plunger boss 10.2, the first plunger boss 10.2 and the plunger rib 10.3 may have a pin comprising the circular cross section shown in FIGS. 16A to 16C or a pin having this shape may be provided elsewhere on the plunger 10.

The guide curve 2.18 comprises a curved section 2.19 slowing down movement of the plunger 10 in the second rotational direction R2 by friction such that the plunger 10 smoothly moves from rotating into translating in the distal direction D instead of rotating, impacting the case 2 and then translating in the distal direction D. In FIG. 16A, the part of the plunger 10, e.g. the first plunger boss 10.2 is being rotated in the second rotational direction R2. In FIG. 16B, said part of the plunger 10 has nearly finished rotating and is guided by the curved section 2.19 from rotating into translating in the distal direction D. In FIG. 16C, said part of the plunger 10 is translating in the distal direction D.

Figure 17A:
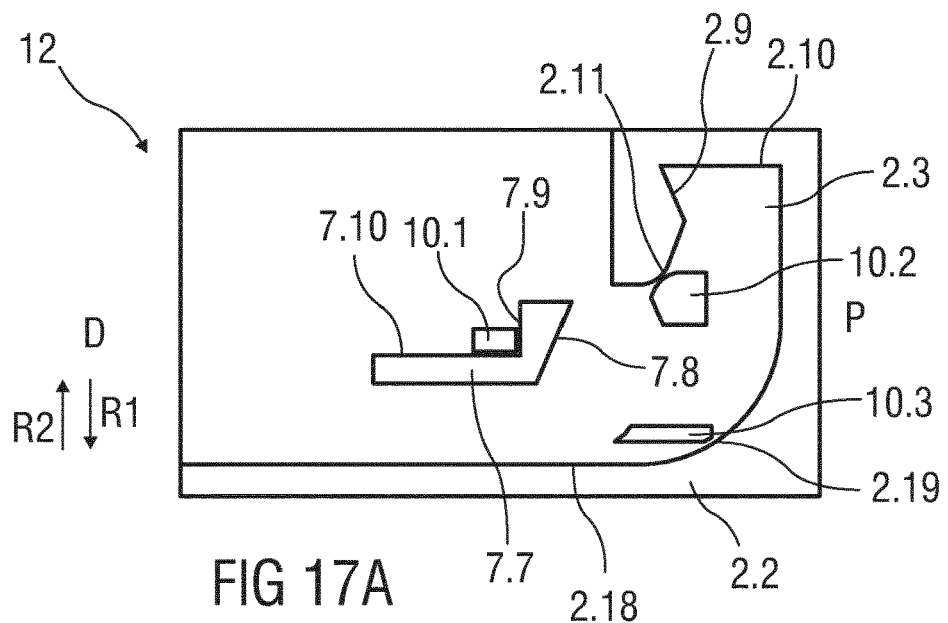
FIGS. 17A to 17C are schematic views of an embodiment of a plunger release mechanism with a guide curve.
Figure 17B:
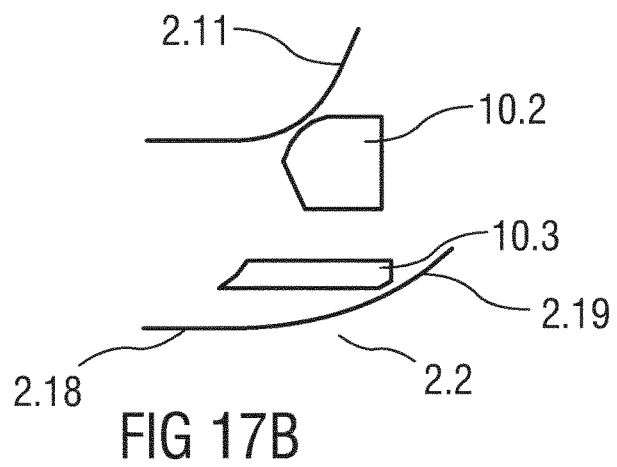
Figure 17C:
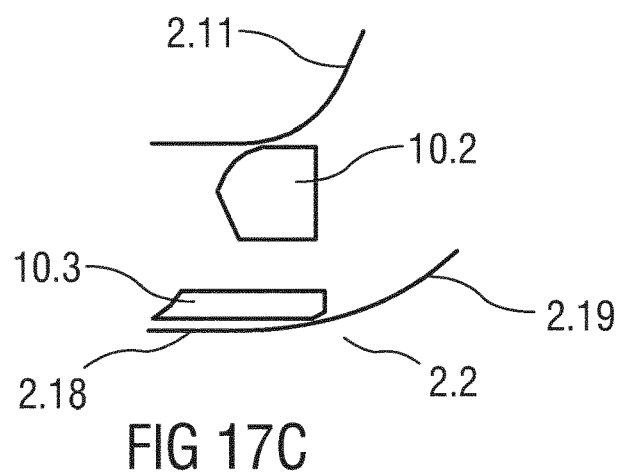
Figure 18:
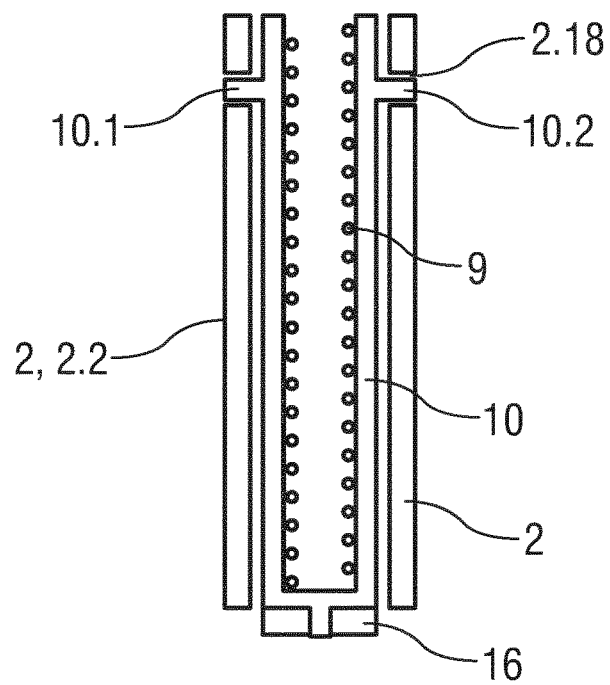
FIG. 18 is a detail view of an embodiment of the drug delivery device.

FIGS. 17A to 17C schematically show the plunger release mechanism 12 with a guide curve 2.18 and a modified first plunger boss 10.2 and a modified case slot 2.3. The guide curve 2.18 engages a part of the plunger 10, e.g. the plunger rib 10.3. The guide curve 2.18 comprises a curved section 2.19 slowing down movement of the plunger 10 in the second rotational direction R2 by friction such that the plunger 10 smoothly moves from rotating into translating in the distal direction D. In FIG. 17A, the part of the plunger 10, e.g. the plunger rib 10.3 is being rotated in the second rotational direction R2. In FIG. 17B, said part of the plunger 10 has nearly finished rotating and is guided by the curved section 2.19 from rotating into translating in the distal direction D. In FIG. 17C, said part of the plunger 10 is translating in the distal direction D. While the first plunger boss 10.2 shown in FIGS. 15A to 15D has a pentagon cross section with relatively sharp corners and the second angled surface 2.11 shown in FIGS. 15A to 15D is angled, the second angled surface 2.11 shown in FIGS. 17A to 17C is rounded off at an end pointing in the second rotational direction R2 thus forming a part of the curved section 2.19 of the guide curve 2.18 and the first plunger boss 10.2 is also rounded off at the one of its corners engaging said end of the second angled surface 2.11 when the plunger 10 is being released. Thus, the audible feedback may be avoided or mitigated while play of the plunger 10 in the first or second rotational direction R1, R2 is limited during translation of the plunger 10 in the axial direction, e.g. the distal direction D and/or the proximal direction P.

The embodiment of FIGS. 17A to 17C may be applied instead of or in addition to the embodiment of FIGS. 16A to 16C.

Figure 19A:
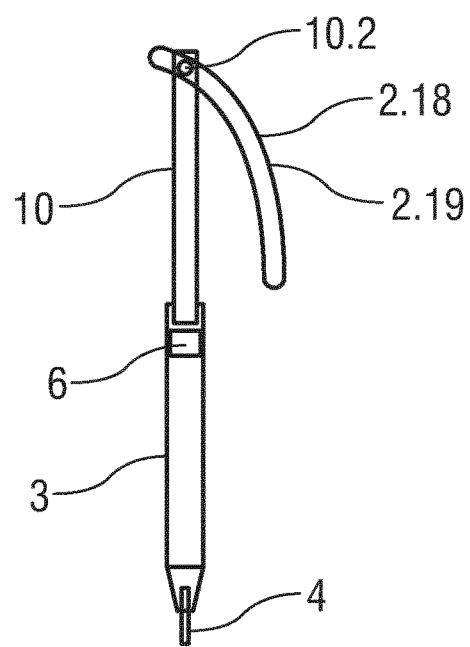
FIGS. 19A to 19C are detail views of an embodiment of the drug delivery device.
Figure 19B:
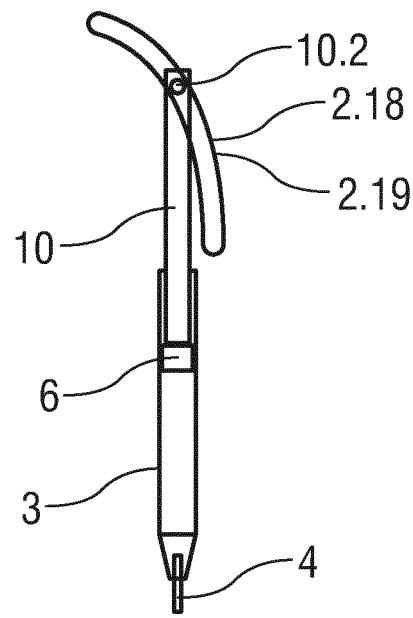
Figure 19C:
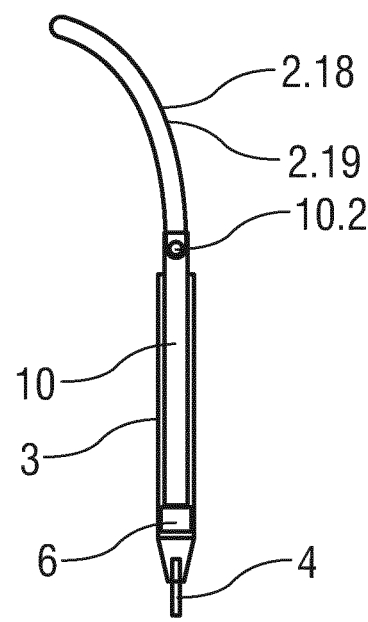

FIGS. 18 and 19A to 19C show detail views of an embodiment of the drug delivery device 1. The plunger 10 comprises one, two or more guide pins. The guide pins may be embodied as one of the second plunger boss 10.1, the first plunger boss 10.2 and the plunger rib 10.3 as shown in one of the FIGS. 5, 6, 7, 11, 14A to 14E, 15A to 15D or the guide pins may be provided in addition to the first plunger boss 10.2, the first plunger boss 10.2 and the plunger rib 10.3. The guide pins are engaged in a guide curve 2.18 which is arranged in the case 2, e.g. in the front case 2.1 or in the rear case 2.2 or in an inner case or in an outer case. In some embodiments, the guide curve 2.18 may be arranged in a sleeve, e.g. in the needle shroud 7. FIGS. 19A to 19C show the guide curve 2.18 in an uncoiled view.

In some embodiments, the plunger 10 or the sleeve, in which the guide curve 2.18 may be arranged, is pivoted. If the plunger 10 is pivoted, a bearing 16 may be arranged on a distal end of the plunger 10 adapted to engage the stopper 6 so as to avoid subjecting the stopper 6 to torque as the plunger 10 is rotated. The guide curve 2.18 comprises a curved section 2.19 extending over such a length of the guide curve 2.18 that the plunger 10 is rotated during most of its translation in the distal direction D. In some embodiments, the guide curve 2.18 may have the shape of a part of a parabola with the guide pin engaged to the vertex of the parabola prior to being released and moving along the parabola away from the vertex when having been released. Due to the long curved extension of the guide curve 2.18, the audible feedback during release of the plunger 10 may be avoided or mitigated. FIG. 19A shows the plunger 10 shortly after having been released. FIG. 19B shows the plunger 10 having travelled in the distal direction D after release. FIG. 19C shows the plunger 10 having at least nearly completely travelled in the distal direction D.

Figure 20A:
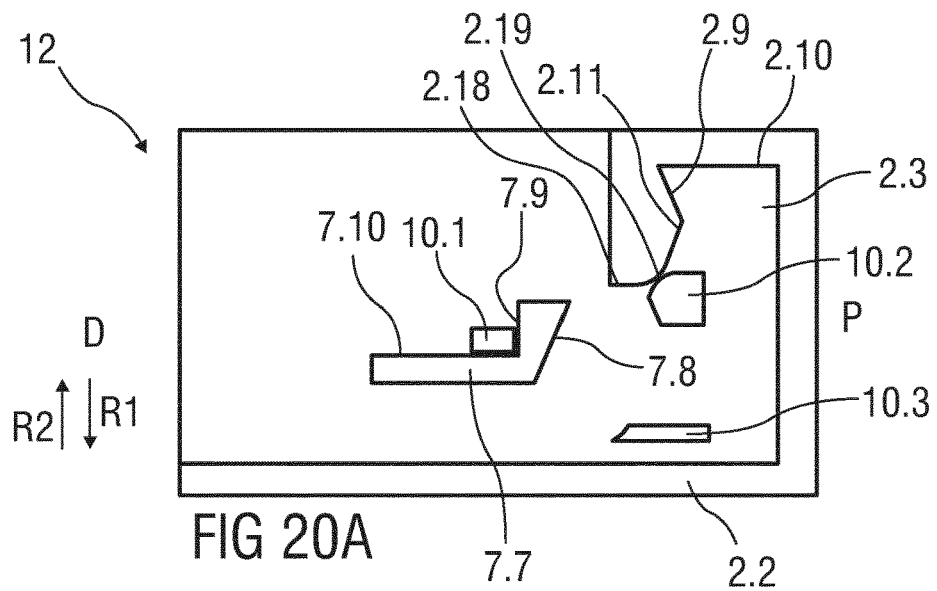
FIGS. 20A to 20C are schematic views of an embodiment of a plunger release mechanism.
Figure 20B:
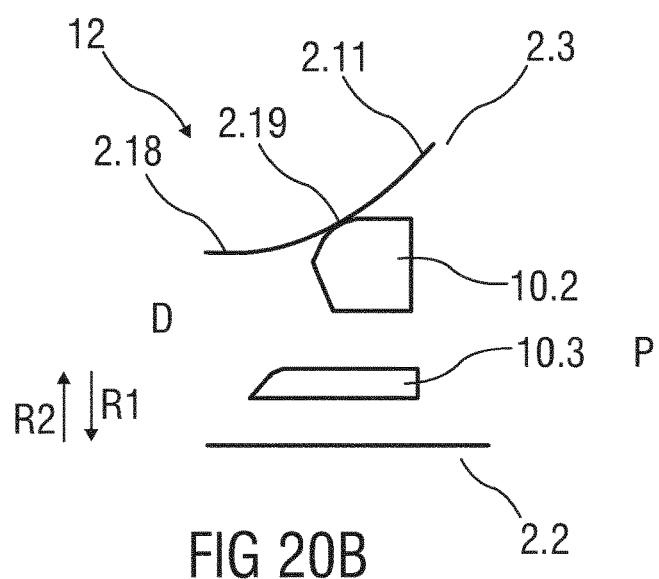
Figure 20C:
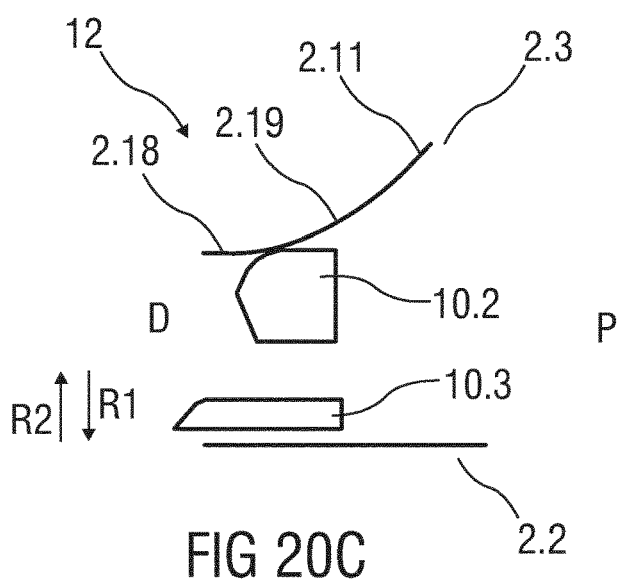

FIGS. 20A to 20C schematically show the plunger release mechanism 12 with a guide curve 2.18 and a modified first plunger boss 10.2 and a modified case slot 2.3. The guide curve 2.18 engages a part of the plunger 10, e.g. the plunger rib 10.3. The guide curve 2.18 comprises a curved section 2.19 slowing down movement of the plunger 10 in the second rotational direction R2 by friction such that the plunger 10 smoothly moves from rotating into translating in the distal direction D. In FIG. 20A, the part of the plunger 10, e.g. the plunger rib 10.3 is being rotated in the second rotational direction R2. In FIG. 20B said part of the plunger 10 has nearly finished rotating and is guided by the curved section 2.19 from rotating into translating in the distal direction D. In FIG. 20C, said part of the plunger 10 is translating in the distal direction D. While the first plunger boss 10.2 shown in FIGS. 15A to 15D has a pentagon cross section with relatively sharp corners and the second angled surface 2.11 shown in FIGS. 15A to 15D is angled, the second angled surface 2.11 shown in FIGS. 20A to 20C is rounded off at an end pointing in the second rotational direction R2 thus forming the curved section 2.19 of the guide curve 2.18 and the first plunger boss 10.2 is also rounded off at the one of its corners engaging said end of the second angled surface 2.11 when the plunger 10 is being released. Thus, the audible feedback may be avoided or mitigated while play of the plunger 10 in the first or second rotational direction R1, R2 is limited during translation of the plunger 10 in the axial direction, e.g. the distal direction D and/or the proximal direction P. The guide curve 2.18 of FIGS. 20A to 20C does therefore comprise a curved section 2.19 with only an inside of the turn but not an outside of the turn whereas the embodiments of FIGS. 16A to 19C comprise both an inside of the turn and an outside of the turn. The curved section 2.19 and the first plunger boss 10.2 may comprise materials increasing friction between the curved section 2.19 and the first plunger boss 10.2 in order to prevent the plunger boss 10.2 from prematurely disengaging the curved section 2.19. Likewise, a radius of the curved section 2.19 may be varied or the curved section 2.19 may be flattened to achieve this.

The embodiments shown in FIGS. 16A to 20C may be applied to all plunger release mechanisms 12 in which a plunger 10 has to be rotated in order to be released for translation in the distal direction D. In particular, the embodiments shown in FIGS. 16A to 20C may be applied to the plunger release mechanism 12 shown in FIGS. 15A to 15D and to the plunger release mechanism shown in in one of the FIGS. 5, 6, 7, 11, 14A to 14E, 15A to 15D and modifications thereof.

In some embodiments, the illustrated drug delivery device may be an autoinjector.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastrointestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholylgamma-glutamyl)-des(B30) human insulin; B29-N-(ω-carboxyheptadecanoyl)-des(B30) humaninsulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigenbinding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a fulllength antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
1.1 control subassembly
1.2 drive subassembly
2 case
2.1 front case
2.2 rear case
2.3 case slot
2.9 first angled surface
2.10 wall
2.11 second angled surface
2.12 stop
2.13 resilient beam
2.14 recess
2.15 radial stop
2.16 transversal surface
2.18 guide curve
2.19 curved section
2.20 curved slot
2.21 curved slot surface
3 syringe
4 needle
5 protective needle sheath
6 stopper
7 needle shroud
7.1 compliant shroud beam
7.6 aperture
7.7 shroud rib
7.8 proximal face
7.9 distal face
7.10 longitudinal face
8 shroud spring
9 drive spring
10 plunger
10.1 second plunger boss
10.2 first plunger boss
10.3 plunger rib
11 cap
11.3 compliant beam
11.4 rib
11.5 grip features
12 plunger release mechanism
14 first shroud lock mechanism
15 second shroud lock mechanism
16 bearing
D distal direction
FEP first extended position
M medicament
P proximal direction
R1 first rotational direction
R2 second rotational direction
RP retracted position
SEP second extended position

The invention claimed is:

1. A drug delivery device, having a longitudinal axis and comprising:
  a plunger release mechanism comprising:
  a plunger movable along the longitudinal axis, wherein the plunger comprises a plunger boss extending radially outwards from the plunger;
  a case comprising a case slot adapted to engage the plunger boss so as to restrict movement of the plunger along the longitudinal axis, wherein the plunger is configured to be rotated such that the plunger boss disengages the case slot thus releasing the plunger for axial translation in a distal direction for dispensing a drug; and
  a guide curve arranged on the case and adapted to engage at least one part of the plunger so as to guide the plunger when the plunger is being released to move along the longitudinal axis in the distal direction for dispensing the drug,
  wherein the guide curve comprises a curved section, wherein the curved section extends over such a length of the guide curve that the plunger is rotated during most of its axial translation, wherein the curved section is arranged to engage at least one part of the plunger one or both of during or after disengagement of the plunger boss from the case slot, and wherein the plunger boss is rounded off at least in a region configured to engage an inside of a turn of the curved section.

2. The drug delivery device of claim 1, wherein the case slot comprises a surface adapted to engage the plunger boss so as to inhibit axial translation.

3. The drug delivery device of claim 2, wherein the surface comprises a rounded off end in a rotational direction, in which the plunger is configured to rotate out of engagement with the case slot such that the rounded off end of the surface forms the inside of the turn of the curved section configured to be engaged by the plunger boss.

4. The drug delivery device of claim 1, wherein the curved section comprises an outside of a turn configured to engage the at least one part of the plunger.

5. The drug delivery device of claim 1, wherein the guide curve is shaped as a part of a parabola.

6. The drug delivery device of claim 5, wherein the at least one part of the plunger is engaged to a vertex of the parabola when the plunger boss of the plunger is engaged in the case slot of the case.

7. The drug delivery device of claim 1, wherein a bearing is arranged on a distal end of the plunger for engaging a stopper of a medicament container.

8. The drug delivery device of claim 1, wherein the surface of the case slot, adapted to engage the plunger boss, is angled so as to induce a torque to the plunger when an axial force is applied to the plunger.

9. The drug delivery device of claim 1, further comprising a medicament container having a stopper adapted to be engaged by the plunger.

10. The drug delivery device of claim 9, wherein the medicament container contains a medicament.

11. The drug delivery device of claim 1, wherein the drug delivery device is an autoinjector.

12. A method of manufacturing a drug delivery device comprising:
providing a plunger movable along a longitudinal axis, wherein the plunger comprises a plunger boss extending radially outwards from the plunger;
providing a case comprising a case slot adapted to engage the plunger boss so as to inhibit or restrict movement of the plunger along the longitudinal axis, wherein the plunger is configured to be rotated such that the plunger boss disengages the case slot thus releasing the plunger for axial translation in a distal direction for dispensing a drug;
providing a guide curve arranged on the case and adapted to engage at least one part of the plunger so as to guide the plunger when the plunger is being released to move along the longitudinal axis in the distal direction for dispensing the drug, wherein the guide curve comprises a curved section, wherein the curved section extends over such a length of the guide curve that the plunger is rotated during most of its axial translation, and wherein the curved section is arranged to engage at least one part of the plunger one or both of during or after disengagement of the plunger boss from the case slot; and
assembling the plunger and the guide curve such that the guide curve engages at least one part of the plunger so as to guide the plunger when the plunger is being released to move along the longitudinal axis.

13. The method of claim 12, comprising:
engaging a surface of the case slot with the plunger boss so as to inhibit axial translation, wherein the surface comprises a rounded off end in a rotational direction.

14. The method of claim 13, comprising:
rotating the plunger out of engagement with the surface of the case slot such that the rounded off end of the surface forms an inside of a turn of the curved section configured to be engaged by the part of the plunger being the plunger boss.

15. The method of claim 12, wherein the guide curve is shaped as a part of a parabola.

16. The method of claim 15, wherein the at least one part of the plunger is engaged to a vertex of the parabola when the plunger boss of the plunger is engaged in the case slot of the case of the drug delivery device.

17. The method of claim 12, wherein a bearing is arranged on a distal end of the plunger for engaging a stopper of a medicament container that contains a medicament.

18. The method of claim 12, wherein the drug delivery device is an autoinjector.

19. A drug delivery device, having a longitudinal axis and comprising:
a plunger release mechanism comprising:
a plunger movable along the longitudinal axis; and
a guide curve adapted to engage at least one part of the plunger so as to guide the plunger when the plunger is being released to move along the longitudinal axis in a distal direction for dispensing a drug, wherein the guide curve comprises a curved section extending over such a length of the guide curve that the plunger is rotated during most of its axial translation, wherein the guide curve is configured such that the at least one part of the plunger is initially maintained in engagement with the guide curve, and wherein the guide curve is configured such that, after initially being engaged with the at least one part of the plunger, the at least one part of the plunger subsequently disengages from the guide curve.

20. The drug delivery device of claim 19, wherein the curved section comprises an outside of a turn configured to engage the at least one part of the plunger.

21. The drug delivery device of claim 19, wherein the guide curve is shaped as a part of a parabola.

22. The drug delivery device of claim 21, wherein the at least one part of the plunger is engaged to a vertex of the parabola when a plunger boss of the plunger is engaged in a case slot of a case.

23. The drug delivery device of claim 19, wherein a bearing is arranged on a distal end of the plunger for engaging a stopper of a medicament container.

24. The drug delivery device of claim 19, wherein the drug delivery device is an autoinjector.

* * * * *

UNITED STATES PATENT AND TRADEMARK OFFICE
CERTIFICATE OF CORRECTION

PATENT NO. : 11,612,695 B2  
APPLICATION NO. : 16/493505  
DATED : March 28, 2023  
INVENTOR(S) : Dasbach et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 513 days.

Signed and Sealed this  
Twentieth Day of May, 2025

Coke Morgan Stewart  
*Acting Director of the United States Patent and Trademark Office*